(12) United States Patent
Shi et al.

(10) Patent No.: US 11,887,303 B2
(45) Date of Patent: Jan. 30, 2024

(54) IMAGE PROCESSING MODEL GENERATION METHOD, IMAGE PROCESSING METHOD AND DEVICE, AND ELECTRONIC DEVICE

(71) Applicants: BEIJING BOE TECHNOLOGY DEVELOPMENT CO., LTD., Beijing (CN); BOE TECHNOLOGY GROUP CO., LTD., Beijing (CN)

(72) Inventors: Yongming Shi, Beijing (CN); Qiong Wu, Beijing (CN); Ge Ou, Beijing (CN); Chun Wang, Beijing (CN)

(73) Assignees: BEIJING BOE TECHNOLOGY DEVELOPMENT CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 417 days.

(21) Appl. No.: 17/423,439

(22) PCT Filed: Aug. 17, 2020

(86) PCT No.: PCT/CN2020/109611
§ 371 (c)(1),
(2) Date: Jul. 15, 2021

(87) PCT Pub. No.: WO2021/032062
PCT Pub. Date: Feb. 25, 2021

(65) Prior Publication Data
US 2022/0114724 A1 Apr. 14, 2022

(30) Foreign Application Priority Data
Aug. 22, 2019 (CN) .......................... 201910778807.0

(51) Int. Cl.
*G16H 30/00* (2018.01)
*G06T 7/10* (2017.01)
(Continued)

(52) U.S. Cl.
CPC ............ *G06T 7/0012* (2013.01); *G06V 10/82* (2022.01); *G16H 30/40* (2018.01);
(Continued)

(58) Field of Classification Search
USPC ............. 382/128–159, 181–224; 704/1–275; 706/1–60, 900–903
See application file for complete search history.

(56) References Cited

U.S. PATENT DOCUMENTS 10,049,451 B2 * 8/2018 Fisher .................. G06T 7/0012
10,468,142 B1 * 11/2019 Abou Shousha ...... G16H 30/20
(Continued)

FOREIGN PATENT DOCUMENTS

| CN | 102525377 A | 7/2012 |
| CN | 106709929 A | 5/2017 |

(Continued)

OTHER PUBLICATIONS

Hodi F Stephen; Compositions and Methods for Identification, Assessment, Prevention, and Treatment of Melanoma Using PD-L1 Isoforms; Jul. 23, 2015 (Year: 2015).*

(Continued)

*Primary Examiner* — Marcellus J Augustin
(74) *Attorney, Agent, or Firm* — IP & T GROUP LLP

(57) ABSTRACT

An image processing model generation method includes: inputting at least one training sample lesion image into an initial image processing model, the initial image processing model including a classification layer and a marking layer; calling the classification layer; calling the marking layer; obtaining a loss value of the at least one training sample lesion image in the initial image processing model; determining whether the loss value is within a preset range; if not, updating parameters of the initial image processing model, an image processing model with updated parameters being (Continued)

used as an initial image processing model in next training; and repeating above steps until the loss value is within the preset range.

20 Claims, 12 Drawing Sheets

(51) Int. Cl.
  *G06T 7/11* (2017.01)
  *G06T 7/33* (2017.01)
  *G06T 7/00* (2017.01)
  *G16H 30/40* (2018.01)
  *G06V 10/82* (2022.01)

(52) U.S. Cl.
  CPC ............... *G06T 2207/20081* (2013.01); *G06T 2207/20084* (2013.01); *G06T 2207/30096* (2013.01)

(56) References Cited

U.S. PATENT DOCUMENTS

| | | | |
|---|---|---|---|
| 2011/0264087 A1* | 10/2011 | Haemmerich | A61B 18/1492 606/33 |
| 2012/0101372 A1 | 4/2012 | Teramura et al. | |
| 2014/0101080 A1* | 4/2014 | Lee | G16H 30/40 706/12 |
| 2015/0003677 A1* | 1/2015 | Cho | G06T 7/0012 382/103 |
| 2017/0161894 A1 | 6/2017 | Fisher | |
| 2019/0188870 A1* | 6/2019 | Park | G06T 7/30 |
| 2021/0118137 A1 | 4/2021 | Shi et al. | |
| 2021/0343016 A1 | 11/2021 | Tian et al. | |

FOREIGN PATENT DOCUMENTS

| | | |
|---|---|---|
| CN | 108564567 A | 9/2018 |
| CN | 108961296 A | 12/2018 |
| CN | 109363698 A | 2/2019 |
| CN | 109671053 A | 4/2019 |
| CN | 110110808 A | 8/2019 |
| CN | 110136809 A | 8/2019 |
| CN | 110490262 A | 11/2019 |
| JP | 2005-339075 A | 12/2005 |
| JP | 2010-067252 A | 3/2010 |
| TW | 201227611 A1 | 7/2012 |

OTHER PUBLICATIONS

Pranav Rajpurkar et al., CheXNet: Radiologist-Level Pneumonia Detection on Chest X-Rays with Deep Learning, Dec. 25, 2017, arXiv:1711.05225v3.

The First Office Action of Priority Application No. CN 201910778807.0 issued by the Chinese Patent Office dated Aug. 31, 2021.

* cited by examiner

IMAGE PROCESSING MODEL GENERATION METHOD, IMAGE PROCESSING METHOD AND DEVICE, AND ELECTRONIC DEVICE

CROSS-REFERENCE TO RELATED APPLICATIONS

This application is a national phase entry under 35 USC 371 of International Patent Application No. PCT/CN2020/109611, filed on Aug. 17, 2020, which claims priority to Chinese Patent Application No. 201910778807.0, filed on Aug. 22, 2019, which are incorporated herein by reference in their entirety.

TECHNICAL FIELD

The present disclosure relates to the field of computer technology, and in particular, to an image processing model generation method, an image processing method, an image processing model generation device, an image processing device, a computer-readable storage medium, and an electronic device.

BACKGROUND

In recent years, with continuous improvement in medical imaging acquisition device and continuous development of subjects such as image processing, pattern recognition, and machine learning, multidisciplinary medical image processing and analysis have become research hotspots.

SUMMARY

In one aspect, an image processing model generation method is provided, and the method includes: inputting at least one training sample lesion image of at least one known disease type into an initial image processing model, the initial image processing model including a classification layer and a marking layer, and each training sample lesion image including coordinates of an initial center point of a lesion region in the training sample lesion image, an initial length of the lesion region, and an initial width of the lesion region; calling the classification layer to perform classification processing on the training sample lesion image, so as to obtain a classification probability of a known disease type corresponding to the training sample lesion image; calling the marking layer to process the training sample lesion image, so as to obtain coordinates of a predicted center point of the lesion region, a predicted length of the lesion region, and a predicted width of the lesion region; obtaining a loss value of the at least one training sample lesion image in the initial image processing model, according to the classification probability corresponding to the training sample lesion image, the coordinates of the initial center point, the initial length, the initial width, the coordinates of the predicted center point, the predicted length, and the predicted width; and determining whether the loss value is within a preset range; if the loss value is not within the preset range, updating parameters of the initial image processing model, an image processing model with the updated parameters being used as an initial image processing model in next training. Above steps are repeated until the loss value is within the preset range, and an image processing model in last training being used as a trained target image processing model.

In some embodiments, calling the classification layer to perform classification processing on the training sample lesion image, so as to obtain the classification probability of the known disease type corresponding to the training sample lesion image includes: inputting at least one group of one-dimensional feature maps of the training sample lesion image into the classification layer; calling the classification layer to perform classification processing on the one-dimensional feature maps; and outputting the classification probability of the known disease type corresponding to the training sample lesion image.

In some embodiments, calling the marking layer to process the training sample lesion image, so as to obtain the coordinates of the predicted center point of the lesion region, the predicted length of the lesion region, and the predicted width of the lesion region includes: inputting a plurality of groups of processed two-dimensional feature maps of the training sample lesion image into the marking layer; calling the marking layer to determine a largest feature point in the two-dimensional feature maps, and a maximum feature value and two-dimensional coordinates of the largest feature point; and determining the coordinates of the predicted center point of the lesion region, the predicted length of the lesion region, and the predicted width of the lesion region, according to the largest feature point, the maximum feature value, the two-dimensional coordinates, and a preset feature threshold.

In some embodiments, the two-dimensional coordinates include a first coordinate in a horizontal axis direction and a second coordinate in a vertical axis direction.

Determining the coordinates of the predicted center point of the lesion region, the predicted length of the lesion region, and the predicted width of the lesion region, according to the largest feature point, the maximum feature value, the two-dimensional coordinates, and the preset feature threshold includes: determining the two-dimensional coordinates as the coordinates of the predicted center point; calculating an absolute value of a feature difference between the maximum feature value and the preset feature threshold; obtaining a first feature point and a second feature point in the horizontal axis direction of the two-dimensional feature maps, and a third feature point and a fourth feature point in the vertical axis direction of the two-dimensional feature maps, according to the absolute value of the feature difference and the two-dimensional coordinates of the largest feature point; obtaining a first coordinate of the first feature point in the horizontal axis direction, and a second coordinate of the second feature point in the horizontal axis direction; obtaining a third coordinate of the third feature point in the vertical axis direction, and a fourth coordinate of the fourth feature point in the vertical axis direction;

Calculating the predicted width, according to the first coordinate and the second coordinate; and calculating the predicted length, according to the third coordinate and the fourth coordinate.

In some embodiments, the initial image processing model further includes: a global average pooling layer. Before the classification layer and the marking layer are called, the method further includes: inputting a plurality of groups of two-dimensional feature maps of the training sample lesion image into the global average pooling layer; and calling the global average pooling layer to perform global average pooling on the plurality of groups of two-dimensional feature maps, so as to obtain a plurality of groups of one-dimensional feature maps corresponding to the plurality of groups of two-dimensional feature maps.

In some embodiments, the initial image processing model further includes a fully-connected layer. After the global average pooling layer is called and before the classification layer is called, the method further includes: calling the fully-connected layer to perform feature extraction on the plurality of groups of one-dimensional feature maps obtained after global average pooling, so as to obtain the at least one group of one-dimensional feature maps of the training sample lesion image. The at least one group of one-dimensional feature maps are input into the classification layer.

In some embodiments, the initial image processing model further includes a feature weighted summation layer and an up-sampling layer. After the global average pooling layer is called, and before the marking layer is called, the method further includes: inputting the plurality of groups of two-dimensional feature maps of the training sample lesion image and the plurality of groups of one-dimensional feature maps obtained after global average pooling into the feature weighted summation layer; calling the feature weighted summation layer to perform, according to the plurality of groups of one-dimensional feature maps, feature weighted summation on each of the plurality of groups of two-dimensional feature maps; and calling the up-sampling layer to perform up-sampling processing on a plurality of groups of two-dimensional feature maps that have been performed with the feature weighted summation, so as to obtain the plurality of groups of processed two-dimensional feature maps of the training sample lesion image; the plurality of groups of processed two-dimensional feature maps being input into the marking layer.

In some embodiments, the initial image processing model further includes a neural network. The neural network includes at least one layer, and each layer sequentially includes a convolutional layer, an activation function layer, and a pooling layer. Before the inputting the plurality of groups of two-dimensional feature maps of the training sample lesion image into the global average pooling layer, the method further includes: inputting the training sample lesion image into the neural network; and calling the neural network to sequentially input the training sample lesion image into the convolutional layer, the activation function layer, and the pooling layer of each layer of the neural network, so as to obtain the plurality of groups of two-dimensional feature maps of the training sample lesion image. The plurality of groups of two-dimensional feature maps are input into the global average pooling layer.

In some embodiments, the obtaining the loss value of the at least one training sample lesion image in the initial image processing model, according to the classification probability corresponding to the training sample lesion image, the coordinates of the initial center point, the initial length, the initial width, the coordinates of the predicted center point, the predicted length, and the predicted width includes: calculating a classification loss value, according to the classification probability corresponding to the training sample lesion image; calculating a position loss value, according to the coordinates of the initial center point, the initial length, the initial width, the coordinates of the predicted center point, the predicted length, and the predicted width that correspond to the training sample lesion image; and obtaining the loss value of the training sample lesion image in the initial image processing model, according to the classification loss value and the position loss value.

In another aspect, an image processing method is provided, the method includes: inputting a lesion image to be processed into a target image processing model; the target image processing model being obtained through training by the method in some of the above embodiments, the target image processing model including a classification layer and a marking layer; calling the classification layer to perform classification processing on the lesion image to be processed, so as to obtain a classification probability of a disease type corresponding to the lesion image to be processed; calling the marking layer to process the lesion image to be processed, so as to obtain coordinates of a region center point of a lesion region included in the lesion image to be processed, a region length of the lesion region, and a region width of the lesion region; determining a disease type corresponding to the lesion image to be processed, according to the classification probability; and determining a lesion marking region in the lesion image to be processed, according to the coordinates of the region center point, the region length, and the region width.

In some embodiments, the calling the classification layer to perform classification processing on the lesion image to be processed, so as to obtain the classification probability of a disease type corresponding to the lesion image to be processed includes: inputting at least one group of one-dimensional feature maps of the lesion image to be processed into the classification layer; calling the classification layer to perform classification processing on the one-dimensional feature maps; and outputting the classification probability of the disease type corresponding to the lesion image to be processed.

In some embodiments, calling the marking layer to process the lesion image to be processed, so as to obtain coordinates of the region center point of the lesion region included in the lesion image to be processed, the region length of the lesion region, and a region width of the lesion region includes: inputting a plurality of groups of processed two-dimensional feature maps of the lesion image to be processed into the marking layer; calling the marking layer to determine a largest feature point in the two-dimensional feature maps, and a maximum feature value and two-dimensional coordinates of the largest feature point; and determining the coordinates of the region center point of the lesion region included in the lesion image to be processed, the region length of the lesion region, and the region width of the region, according to the largest feature point, the maximum feature value, the two-dimensional coordinates, and a preset feature threshold.

In some embodiments, the two-dimensional coordinates include a first coordinate in a horizontal axis direction and a second coordinate in a vertical axis direction. Determining the coordinates of the region center point of the lesion region included in the lesion image to be processed, the region length of the region, and the region width of the lesion region, according to the largest feature point, the maximum feature value, the two-dimensional coordinates, and the preset feature threshold includes: determining the two-dimensional coordinates as the coordinates of the region center point; calculating an absolute value of a feature difference between the maximum feature value and the preset feature threshold; obtaining a first feature point and a second feature point in the horizontal axis direction of the two-dimensional feature maps, and a third feature point and a fourth feature point in the vertical axis direction of the two-dimensional feature maps, according to the absolute value of the feature difference and the two-dimensional coordinates of the largest feature point; obtaining a first coordinate of the first feature point in the horizontal axis direction, and a second coordinate of the second feature point in the horizontal axis direction; obtaining a third coordinate of the third feature point in the vertical axis direction, and a fourth coordinate of the fourth feature point in the vertical axis direction; calculating the region width, according to the first coordinate and the second coordinate; and calculating the region length, according to the third coordinate and the fourth coordinate.

In yet another aspect, a non-transitory computer-readable storage medium is provided. The computer-readable storage medium stores computer program instructions. The computer program instructions, when executed by a processor, cause the processor to perform one or more steps in the image processing model generation method as described in some of the above embodiments, and/or one or more steps in the image processing method as described in some of the above embodiments.

In yet another aspect, a computer program product is provided. The computer program product includes computer program instructions stored in non-transitory computer-readable storage medium. When executed on a computer, the computer program instructions cause the computer to perform one or more steps in the image processing model generation method as described in some of the above embodiments, and/or one or more steps in the image processing method as described in some of the above embodiments.

In yet another aspect, a computer program is provided. When executed on a computer, the computer program causes the computer to perform one or more steps in the image processing model generation method as described in some of the above embodiments, and/or one or more steps in the image processing method as described in some of the above embodiments.

In yet another aspect, an electronic device is provided, including a processor, a memory, and a computer program that is stored in the memory and executable on the processor. When the computer program is executed by the processor, one or more steps in the image processing model generation method as described in some of the above embodiments, and/or one or more steps in the image processing method as described in some of the above embodiments are implemented.

BRIEF DESCRIPTION OF THE DRAWINGS

In order to describe technical solutions in the present disclosure more clearly, accompanying drawings to be used in some embodiments of the present disclosure will be introduced briefly. However, the accompanying drawings to be described below are merely accompanying drawings of some embodiments of the present disclosure. Those of ordinary skill in the art may obtain other drawings according to those drawings. In addition, the accompanying drawings in the following description may be regarded as schematic diagrams, and are not limitations on actual sizes of products, actual processes of methods, and actual timings of signals involved in the embodiments of the present disclosure.

DETAILED DESCRIPTION

Figure 1:
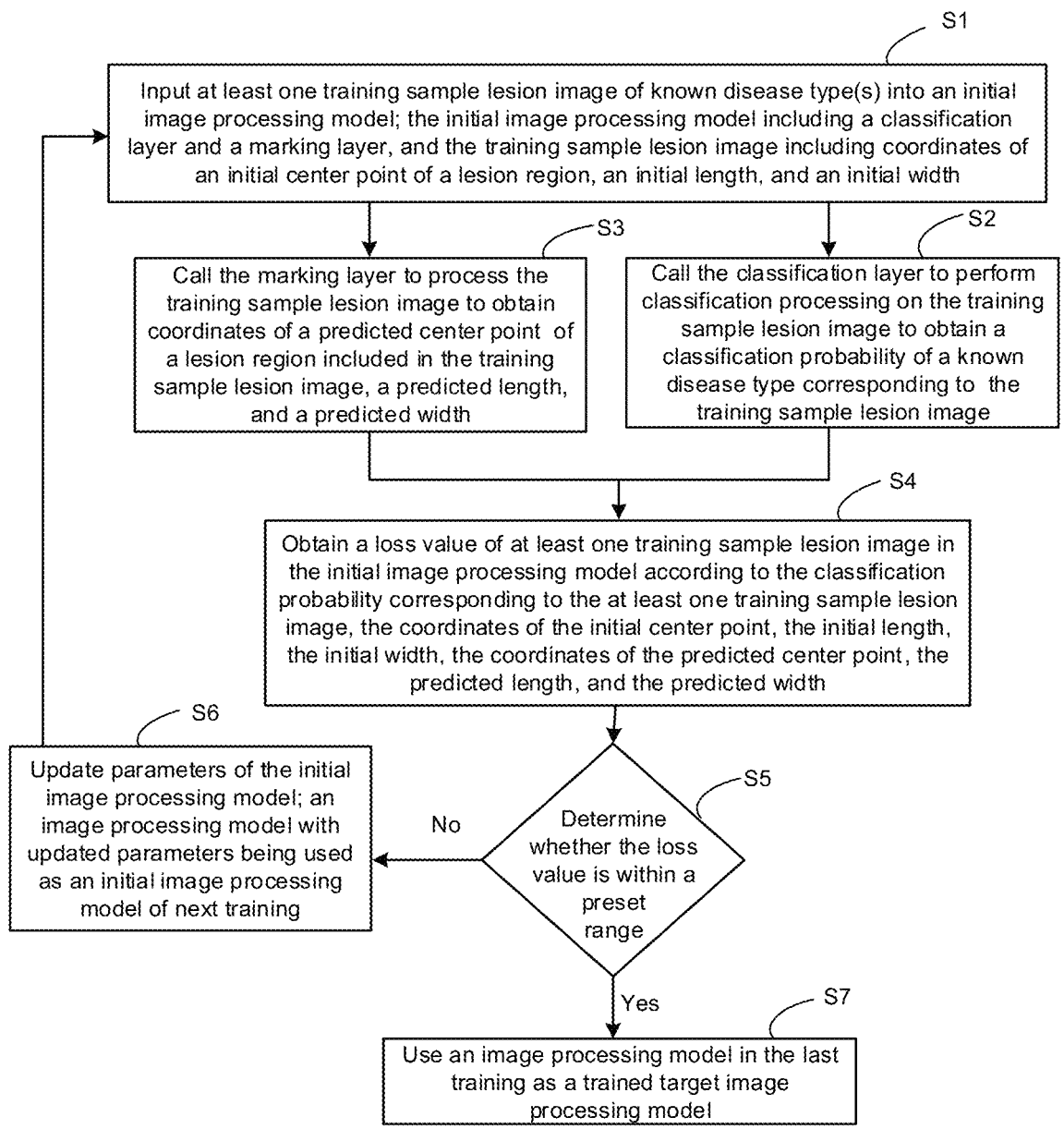
FIG. 1 is a flow diagram of an image processing model generation method, in accordance with some embodiments.

The technical solutions in some embodiments of the present disclosure will be described clearly and completely with reference to accompanying drawings. However, the described embodiments are merely some but not all embodiments of the present disclosure. All other embodiments obtained on the basis of the embodiments provided in the present disclosure by a person of ordinary skill in the art shall be included in the protection scope of the present disclosure.

Unless the context requires otherwise, throughout the description and claims, the term "comprise" and other forms thereof such as the third-person singular form "comprises" and the present participle form "comprising" are construed as an open and inclusive meaning, i.e., "including, but not limited to." In the description, the terms such as "one embodiment," "some embodiments," "exemplary embodiments," "example," "specific example," or "some examples" are intended to indicate that specific features, structures, materials or characteristics related to the embodiment(s) or the example(s) are included in at least one embodiment or example of the present disclosure. Schematic representations of the above terms do not necessarily refer to the same embodiment(s) or example(s). In addition, the specific features, structures, materials or characteristics may be included in any one or more embodiments or examples in any suitable manner.

Below, the terms such as "first" and "second" are only used for descriptive purposes, and are not to be construed as indicating or implying the relative importance or implicitly indicating the number of indicated technical features. Thus, features defined as "first" and "second" may explicitly or implicitly include one or more of the features. In the description of the embodiments of the present disclosure, term "a/the plurality of/multiple" means two or more unless otherwise specified.

Some embodiments may be described using the expression "coupled" and "connected" along with their derivatives. For example, term "connected" may be used in the description of some embodiments to indicate that two or more components are in direct physical or electrical contact with each other. As another example, term "coupled" may be used in the description of some embodiments to indicate that two or more components are in direct physical or electrical contact. The term "coupled" or "communicatively coupled", however, may also mean that two or more components are not in direct contact with each other, but yet still cooperate or interact with each other. The embodiments disclosed herein are not necessarily limited to the content herein.

"A and/or B" includes the following three combinations: only A, only B, and a combination of A and B.

As used herein, the term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]" depending on the context.

The use of "adapted to" or "configured to" herein is meant open and inclusive language that does not exclude devices adapted to or configured to perform additional tasks or steps.

Additionally, the use of "based on" is meant to be open and inclusive, in that a process, step, calculation, or other action "based on" one or more recited conditions or values may, in practice, be based on additional conditions or value beyond those recited.

In the related art, a disease type may be well diagnosed according to classification algorithms based on deep learning. However, it is found in research that there is a certain difference between a region determined in medicine and an attention region that is used to determine disease in a process of using these classification algorithms to process a medical image. Although some algorithms may be used to substantially mark a position of a lesion on the medical image, this marking manner is too rough to reflect the specific position of the lesion on a pathological tissue.

Based on this, some embodiments of the present disclosure provide an image processing model generation method. As shown in FIG. 1, the method includes the following steps (S1 to S7).

Figure 2:
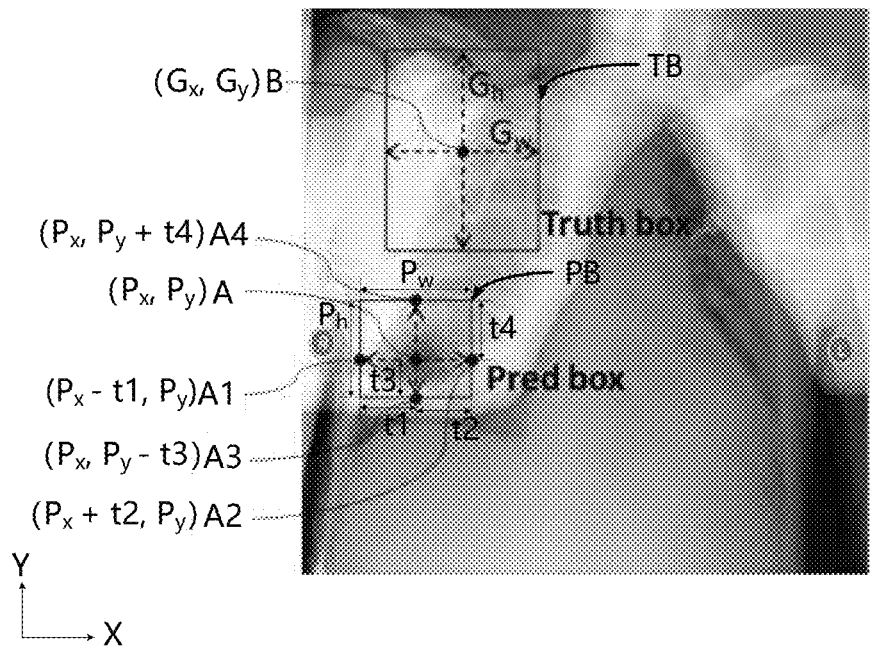
FIG. 2 is a schematic diagram of a training sample lesion image, in accordance with some embodiments.

In S1, at least one training sample lesion image of known disease type(s) is input into an initial image processing model 1 (as shown in FIG. 2).

Figure 3:
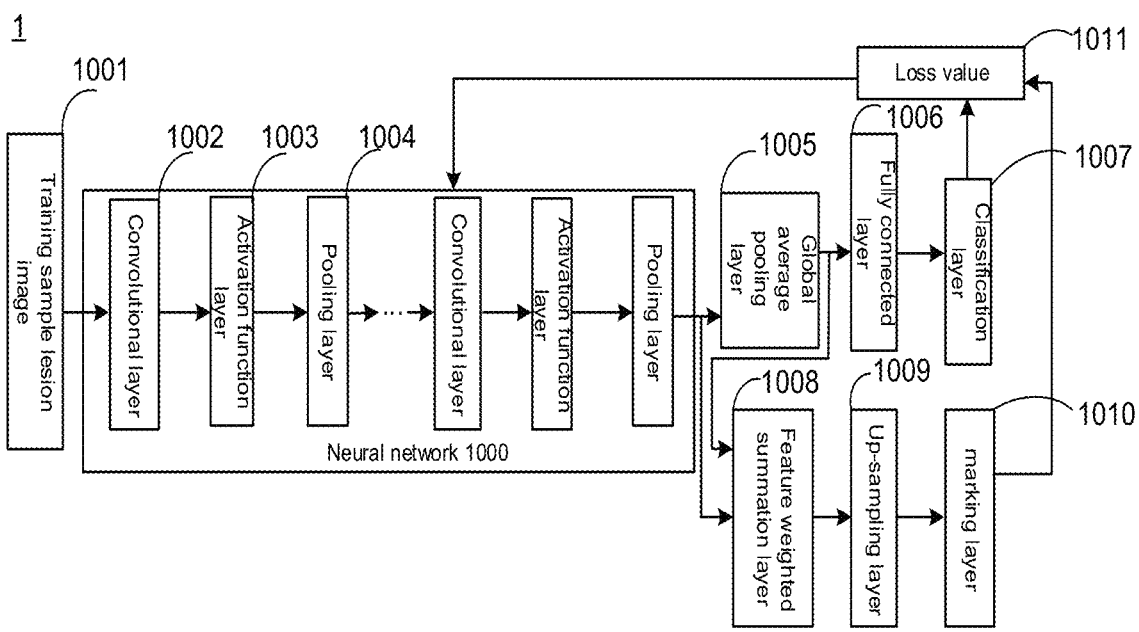
FIG. 3 is a structural diagram of an initial image processing model, in accordance with some embodiments.

As shown in FIGS. 2 and 3, the initial image processing model 1 includes a classification layer 1007 and a marking layer 1010. The training sample lesion image 1001 includes coordinates $(G_x, G_y)$ of an initial center point B of a lesion region, an initial length $G_h$ of the lesion region, and an initial width $G_w$ of the lesion region.

In the embodiments of the present disclosure, the initial image processing model 1 refers to an image processing model that has not been trained or is being trained in a process of training. The known disease type refers to a disease type corresponding to the training sample lesion image 1001. For example, the known disease type may be a disease such as pneumonia, heart disease, or cirrhosis, or the known disease type may be other disease type, depending on specific needs.

The initial image processing model 1 includes the classification layer 1007 and the marking layer 1010. Both the classification layer 1007 and the marking layer 1010 are network layers that may process lesion images.

In a case where the initial image processing model 1 is trained using the training sample lesion image 1001, at least one training sample lesion image 1001 of the known disease type may be obtained. The at least one training sample lesion image 1001 is input into the initial image processing model 1 to train the initial image processing model 1.

A number of the training sample lesion images 1001 input into the initial image processing model 1 may be one or more, such as 500, 800, or 1000, or may also be determined according to actual situations, which is not particularly limited in the embodiments of the present disclosure.

The training sample lesion image 1001 includes a lesion region. The lesion region refers to a position of a lesion in the training sample lesion image 1001, which is expressed by a range having certain area in the training sample lesion image 1001.

For example, the lesion region may be expressed by a rectangular region, and the lesion region may be a true lesion region marked in advance in the training sample lesion image 1001 by a doctor or the like. As shown in FIG. 2, the true lesion region in the training sample lesion image 1001 is a region shown by a truth box TB, which is obtained according to the coordinates $(G_x, G_y)$ of the initial center point B, the initial length $G_h$, and the initial width $G_w$. The coordinates $(G_x, G_y)$ of the initial center point B are coordinates of a center point of the true lesion region in an image coordinate system corresponding to the training sample lesion image 1001. The initial length $G_h$ and the initial width $G_w$ are a length and a width of the true lesion region, respectively.

The above examples are only examples used to better understand the technical solutions of the embodiments of the present disclosure, and should not be taken as the limitations that only imposed on the embodiments of the present disclosure.

After the at least one training sample lesion image 1001 of the known disease type is obtained, the training sample lesion images 1001 may be sequentially input into the initial image processing model 1 to train the initial image processing model 1, and S2 is performed.

In S2, the classification layer 1007 is called to perform classification processing on a training sample lesion image 1001, so as to obtain a classification probability of a known disease type corresponding to the training sample lesion image 1001.

The classification layer 1007 is a network layer that may be used to classify the disease types corresponding to the lesion image(s), and the classification probabilities of various disease types corresponding to the lesion image(s) may be obtained through the classification layer 1007, thereby obtaining the disease type corresponding to the lesion image, such as pneumonia, heart disease, etc.

The training sample lesion image(s) 1001 may include only a lesion of one disease, or may include lesions of a plurality of diseases. For example, the training sample lesion image(s) 1001 include lesions of three diseases, and the classification layer 1002 may obtain classification probabilities of the three diseases corresponding to the training sample lesion image(s) 1001. According to the classification probability of each of the diseases, the type of a disease included in the training sample lesion image 1001 is determined.

In S3, the marking layer 1010 is called to process the training sample lesion image 1001, so as to obtain coordinates of a predicted center point of the lesion region included in the training sample lesion image 1001, a predicted length of the lesion region, and a predicted width of the lesion region.

The marking layer 1010 is a network layer that may be used to mark a specific position of a lesion on a pathological tissue, and the marking layer 1010 may add a marking box to the lesion region on the lesion image, for example the marking box may be a rectangular box, a circular box, or the like.

As shown in FIG. 2, the training sample lesion image 1001 is input into the initial image processing model 1, and after the training sample lesion image 1001 is processed by the marking layer 1010, a prediction box PB is output. The prediction box PB is obtained according to coordinates ($P_x$, $P_y$) of a predicted center point A, a predicted length $P_h$, and a predicted width $P_w$. The coordinates ($P_x$, $P_y$) of the predicted center point A are coordinates of a center point of a predicted lesion region in the image coordinate system corresponding to the training sample lesion image 1001. The predicted length $P_h$ and the predicted width $P_w$ are a length and a width of the predicted lesion region, respectively.

It will be noted that there is no limitation on the order of performing S2 and S3. S2 and S3 may be performed simultaneously, or S2 is performed firstly and S3 is performed then, or S3 is performed firstly and S2 is performed then.

After the classification probability of the disease type and prediction data of the lesion region of the training sample lesion image 1001 may be obtained respectively through S2 and S3, S4 is performed.

In S4, a loss value of at least one training sample lesion image 1001 in the initial image processing model 1 is obtained according to the classification probability correspond to the at least one training sample lesion image 1001, the coordinates ($G_x$, $G_y$) of the initial center point B, the initial length $G_h$, the initial width $G_w$, the coordinates ($P_x$, $P_y$) of the predicted center point A, the predicted length $P_h$, and the predicted width $P_w$. The loss value is denoted as L.

The loss value L may be calculated according to the classification probability correspond to the training sample lesion image 1001, the coordinates ($G_x$, $G_y$) of the initial center point B, the initial length $G_h$, the initial width $G_w$, the coordinates ($P_x$, $P_y$) of the predicted center point A, the predicted length $P_h$, and the predicted width $P_w$.

In some embodiments, a input of one training sample lesion image 1001 is performed during a training process. For a disease in a training sample lesion image 1001, a loss value L is obtained. If the training sample lesion image 1001 includes a plurality of diseases, weighted summation is performed on corresponding loss values according to weights of the plurality of diseases, an average of loss values corresponding to the plurality of diseases in the training sample lesion image 1001 is calculated, and the loss value L of the training sample lesion image 1001 is then obtained.

In some embodiments, a input of a plurality of training sample lesion images 1001 are performed during a training process, and a loss value L of each training sample lesion image 1001 is obtained by using the method in the above embodiment, and the loss value L of the plurality of training sample lesion images 1001 may be obtained by averaging the loss values L of the plurality of training sample lesion images 1001.

After the loss value of the training sample lesion images are obtained through S4, S5 is performed, as shown in FIG. 3.

In S5, whether the loss value L is within a preset range is determined; if the loss value L is not within the preset range, S6 is performed; and if the loss value L is within the preset range, S7 is performed.

In S6, parameters of the initial image processing model 1 are updated, and an image processing model with updated parameters is used as an initial image processing model 1 in the next training.

Figure 8:
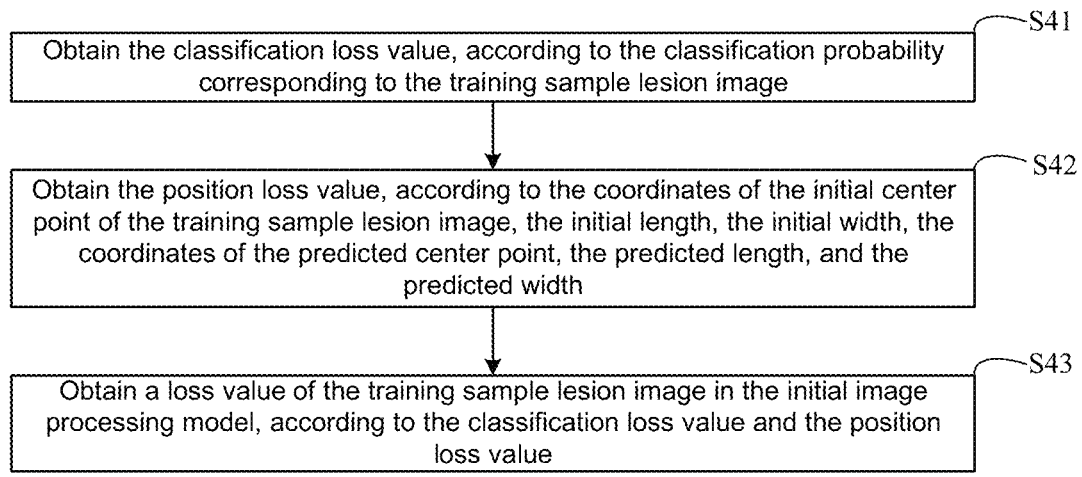

S1 to S5 are repeated until the loss value L is within the preset range, and an image processing model in the last training is used as a trained target image processing model 2 (as shown in FIG. 8).

In S7, an image processing model that is being trained currently (i.e., the image processing model in the last training) is used as the trained target image processing model 2.

In S6 and S7, the preset range refers to a range to be compared with the loss value L, which is a numerical range set in advance.

If the loss value L is within the preset range, it means that current training result of the image processing model has reached an expected result, and the image processing model that is being trained currently (i.e., the image processing model in last training) may be used as the trained target image processing model 2.

When the loss value L is not within the preset range, it means that the training result of the initial image processing model 1 do not meet expectations. Based on the result of the loss value L, there is a need to update the parameters of the initial image processing model 1. The image processing model with the updated parameters is used as the initial image processing model 1 in the next training, and the at least one training sample lesion image 1001 of the known disease type is continued to be input to train the initial image processing model 1.

The image processing model generated by the image processing model generation method provided by the embodiments of the present disclosure may accurately identify the lesion region in the lesion image, and add corresponding marking coordinates, which can reflect the specific position of the lesion on the pathological tissue. An attention region (i.e., the marked lesion region) of the image processing model is trained by the classification layer 1007 and the marking layer 1010, so that the position of the marked lesion region is accurate. The use of the trained image processing model may automatically identify the disease type included in the medical images and mark the positions of the lesion regions of various disease types, which saves manpower and improves efficiency. In addition, the generated image processing model has high detection accuracy in classifying and marking the disease type.

In some embodiments, as shown in FIG. 3, the initial image processing model 1 further includes: a neural network 1000. The neural network 1000 includes at least one layer, and each layer includes a convolutional layer 1002, an activation function layer 1003, and a pooling layer 1007.

Figure 4:
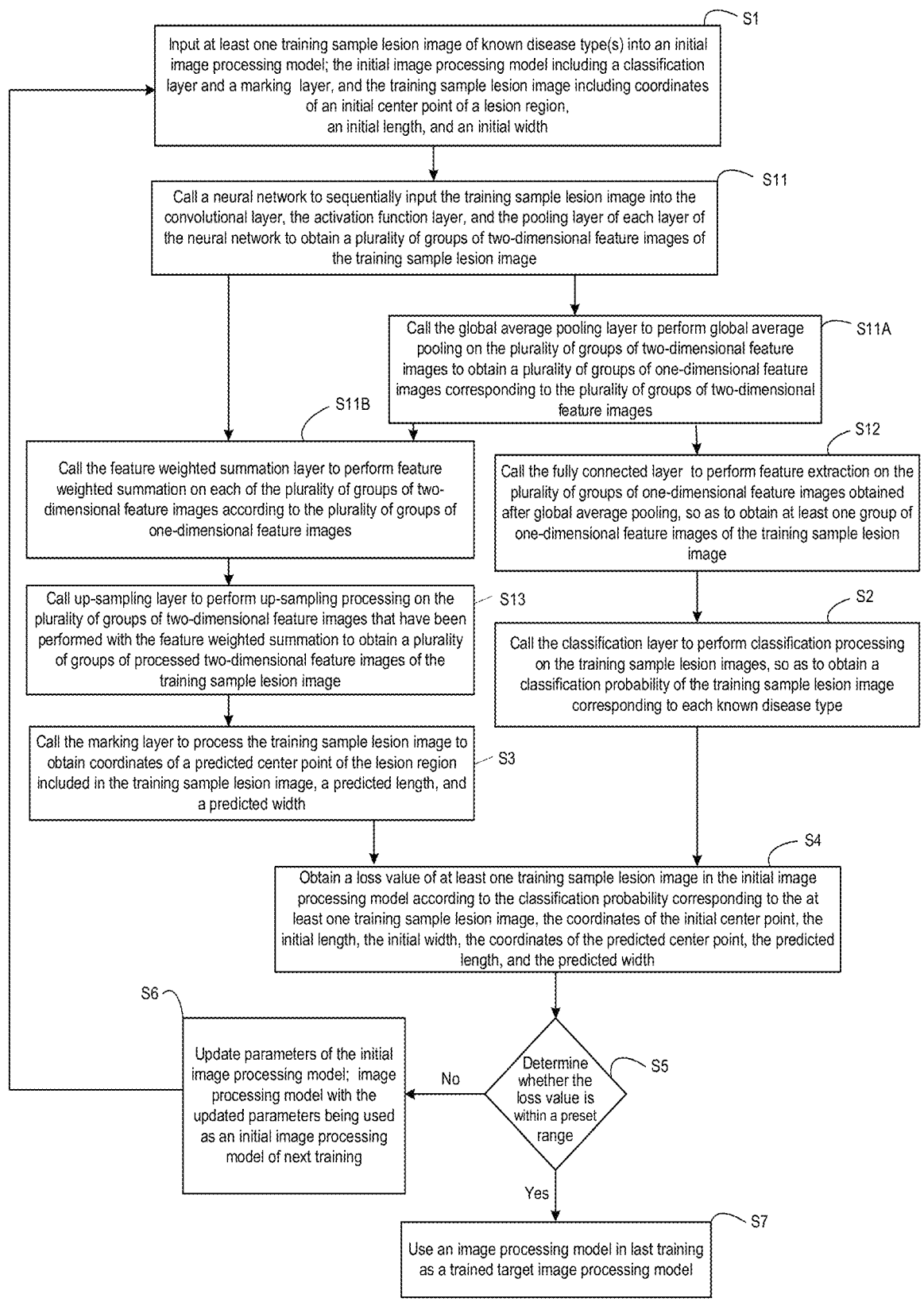
FIG. 4 is a flow diagram of another image processing model generation method, in accordance with some embodiments.

As shown in FIG. 4, the image processing model generation method in the embodiments of the present disclosure further includes: performing step 11 (S11) after S1.

In S11, the neural network 1000 is called to sequentially input the training sample lesion image 1001 into the convolutional layer 1002, the activation function layer 1003, and the pooling layer 1004 of each layer of the neural network 1000 to obtain a plurality of groups of two-dimensional feature maps of the training sample lesion image 1001.

The convolutional layer 1002 is used to extract features; the activation function layer 1003 is used to activate the extracted features; the pooling layer 1004 is used to downsample the activated features, the plurality of groups of two-dimensional feature maps of the training sample lesion image 1001 may be obtained through multi-layer superposition.

In some embodiments, the neural network 1000 in the above-mentioned embodiments of the present disclosure may be a convolutional neural network (CNN), a recurrent neural network (RNN), etc.

In some embodiments, the neural network 1000 in the above-mentioned embodiments of the present disclosure may be a long short term memory network (LSTM), an artificial neural network (ANN), etc.

In some embodiments, as shown in FIG. 3, the initial image processing model 1 further includes: a global average pooling (GAP) layer 1005.

As shown in FIG. 4, the image processing model generation method in the embodiments of the present disclosure further includes: performing step 11A (S11A) after S1.

In S11A, the global average pooling layer 1005 is called to perform global average pooling on the plurality of groups of two-dimensional feature maps, so as to obtain a plurality of groups of one-dimensional feature maps corresponding to the plurality of groups of two-dimensional feature maps.

The plurality of groups of two-dimensional feature maps obtained by the training sample lesion image 1001 through the neural network 1000 are input into the global average pooling layer 1005, and the global average pooling layer 1005 is called to perform global average pooling on the plurality of groups of two-dimensional feature maps to obtain the plurality of groups of one-dimensional feature maps corresponding to the plurality of groups of two-dimensional feature maps.

In some embodiments, as shown in FIG. 3, the initial image processing model 1 further includes a fully-connected layer 1006.

As shown in FIG. 4, the image processing model generation method in the embodiments of the present disclosure further includes: performing step 12 (S12) after S11A.

In S12, the fully-connected layer 1006 is called to perform feature extraction on the plurality of groups of one-dimensional feature maps obtained after global average pooling, so as to obtain at least one group of one-dimensional feature maps of the training sample lesion image 1001.

The plurality of groups of one-dimensional feature maps of the training sample lesion image 1001 which are obtained through processing of the global average pooling layer 1005 are input into the fully-connected layer 1006. The fully-connected layer 1006 is called to perform feature extraction on the plurality of groups of one-dimensional feature maps obtained after global average pooling, so as to obtain the at least one group of one-dimensional feature maps of the training sample lesion image 1001. The at least one group of one-dimensional feature maps are input into the classification layer 1007.

Figure 5:
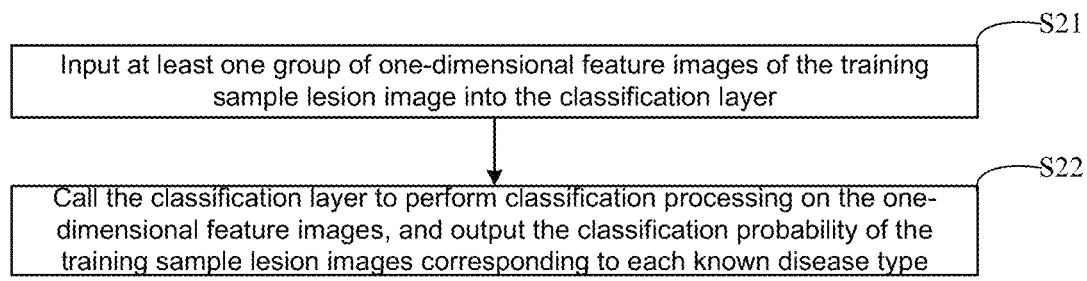
FIGS. 5 to 8 are flow diagrams of S2, S3, S33, and S4 respectively in an image processing model generation method, in accordance with some embodiments.

In some embodiments, as shown in FIG. 5, that the classification layer 1007 is called to perform classification processing on the training sample lesion image 1001 to obtain a classification probability of the known disease type corresponding to the training sample lesion images 1001 in S2 includes steps 21 to 22 (S21 to S22).

In S21, the at least one group of one-dimensional feature maps of the training sample lesion image 1001 is input into the classification layer 1007.

In S22, the classification layer 1007 is called to perform classification processing on the one-dimensional feature maps, and to output the classification probability of the known disease type corresponding to the training sample lesion images 1001.

In some embodiments, as shown in FIG. 3, the initial image processing model 1 further includes a feature weighted summation (FWS) layer 1008 and an up-sampling layer 1009.

As shown in FIG. 4, the image processing model generation method in the embodiments of the present disclosure further includes: performing step 11B (S11B) after S11.

In S11B, the feature weighted summation layer 1008 is called to perform, according to the plurality of groups of one-dimensional feature maps, feature weighted summation on each of the plurality of groups of two-dimensional feature maps.

The plurality of groups of two-dimensional feature maps of the training sample lesion image 1001 and the plurality of groups of one-dimensional feature maps obtained after global average pooling are input into the feature weighted summation layer 1008. The feature weighted summation layer 1008 is called to perform, according to the plurality of groups of one-dimensional feature maps, feature weighted summation on each of the plurality of groups of two-dimensional feature maps.

Step 13 (S13) is performed after S11B.

In S13, the up-sampling layer 1009 is called to perform up-sampling processing on the plurality of groups of two-dimensional feature maps that have been performed to with the feature weighted summation, so as to obtain a plurality of groups of processed two-dimensional feature maps of the training sample lesion image 1001.

Figure 6:
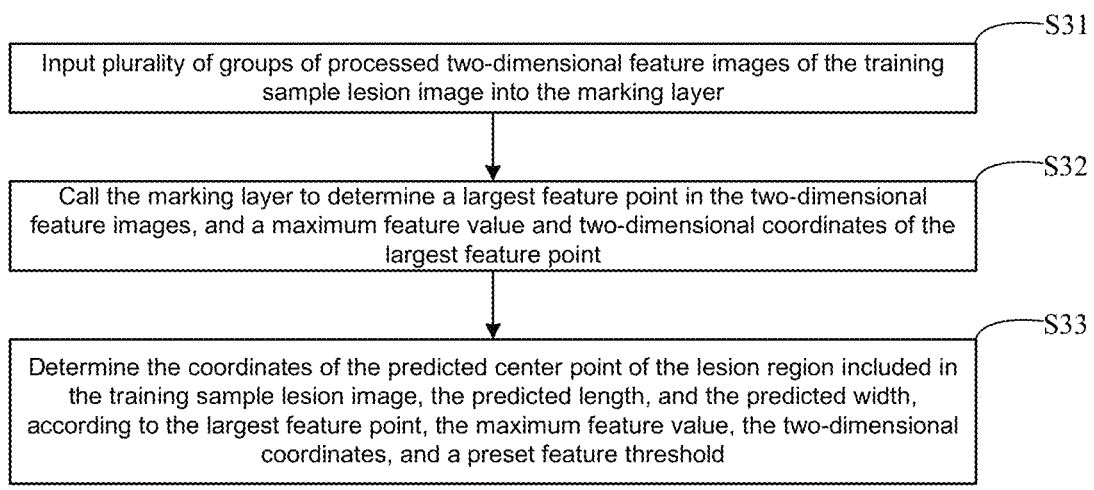

In some embodiments, as shown in FIGS. 2 and 6, S3 includes steps 31 to 33 (S31 to S33), and in S3, the marking layer 1010 is called to process the training sample lesion image 1001 to obtain coordinates ($P_x$, $P_y$) of a predicted center point A, a predicted length $P_h$, and a predicted width $P_w$ of the lesion region included in the training sample lesion image 1001.

In S31, the plurality of groups of processed two-dimensional feature maps of the training sample lesion image 1001 are input into the marking layer 1010.

In S32, the marking layer 1010 is called to determine a largest feature point in the two-dimensional feature maps, and a maximum feature value and two-dimensional coordinates of the largest feature point.

In S33, the coordinates ($P_x$, $P_y$) of the predicted center point A of the lesion region included in the training sample lesion image 1001, the predicted length $P_h$ of the lesion region, and the predicted width $P_w$ of the lesion region are determined according to the largest feature point, the maximum feature value, the two-dimensional coordinates, and a preset feature threshold.

The preset feature threshold may be adjusted according to expected ranges of the predicted length $P_h$ and the predicted width $P_w$ of the lesion region. In general, the larger the preset feature threshold is, the larger the predicted length $P_h$ and the predicted width $P_w$ of the lesion region that are obtained will be, and vice versa.

Figure 7:
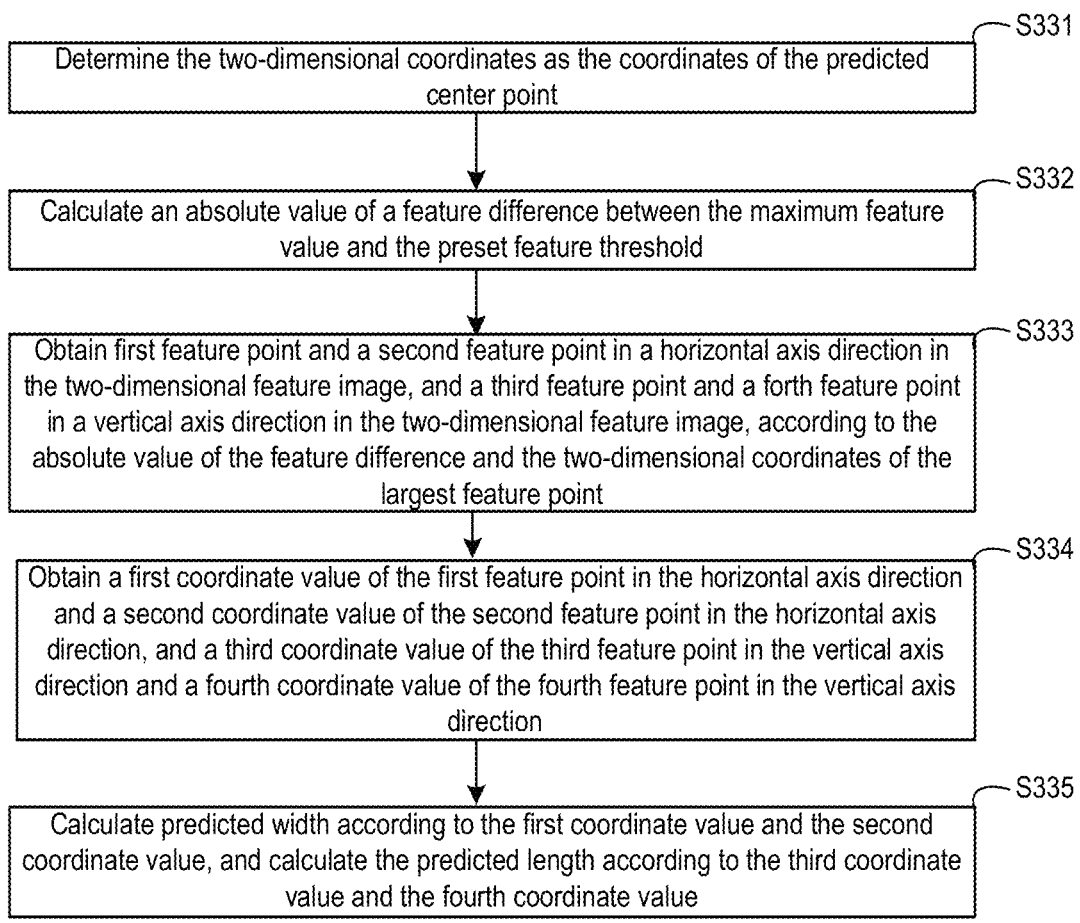

For example, as shown in FIG. 7, in S33, that the coordinates ($P_x$, $P_y$) of the predicted center point A of the lesion region included in the training sample lesion image 1001, the predicted length $P_h$ of the lesion region, and the predicted width $P_w$ of the lesion region are determined according to the largest feature point, the maximum feature value, the two-dimensional coordinates, and a preset feature threshold includes steps 331 to 335 (S331 to S335).

Referring to FIG. 2, in S331, the two-dimensional coordinates of the largest feature point are determined as the coordinates ($P_x$, $P_y$) of the predicted center point A.

In S332, an absolute value of a feature difference between the maximum feature value and the preset feature threshold is calculated.

In S333, a first feature point A1 and a second feature point A2 in a horizontal axis X direction in the two-dimensional feature map, and a third feature point A3 and a forth feature point A4 in a vertical axis Y direction in the two-dimensional feature map are obtained according to the absolute value of the feature difference and the two-dimensional coordinates of the largest feature point.

In S334, a first coordinate ($P_x$−t1) of the first feature point A1 in the horizontal axis X direction and a second coordinate ($P_x$+t2) of the second feature point A2 in the horizontal axis X direction are obtained, and both t1 and t2 are not less than zero. A third coordinate ($P_y$−t3) of the third feature point A3 in the vertical axis Y direction and a fourth coordinate ($P_y$+t4) of the fourth feature point A4 in the vertical axis Y direction are obtained, and both t3 and t4 are not less than zero.

In S335, the predicted width $P_w$ ($P_w$=t2+t1) is obtained according to the first coordinate ($P_x$−t1) and the second coordinate ($P_x$+t2), and the predicted length $P_h$ ($P_h$=t4+t3) is obtained according to the third coordinate ($P_y$−t3) and the fourth coordinate ($P_y$+t4).

In some embodiments, as shown in FIG. 8, in S4, that the loss value L of at least one training sample lesion image 1001 in the initial image processing model 1 is obtained according to the classification probability of the at least one training sample lesion image 1001, the coordinates ($G_x$, $G_y$) of the initial center point B, the initial length $G_h$, the initial width $G_w$, the coordinates ($P_x$, $P_y$) of the predicted center point A, the predicted length $P_h$, and the predicted width $P_w$ includes steps 41 to 43 (S41 to S43).

The loss value L includes a classification loss value and a position loss value.

In S41, the classification loss value is obtained according to the classification probability of the training sample lesion image 1001.

The classification loss value refers to a classification loss existing in a classification probability that is obtained during the classifying of the training sample lesion image 1001 by the initial image processing model 1, and the classification loss value is denoted as $L_{cls}$.

After the classification probability corresponding to the training sample lesion image 1001 is obtained, the classification loss value $L_{cls}$ may be obtained according to each classification probability. In the present disclosure, the classification loss value $L_{cls}$ may be calculated by using softmax, support vector machine (SVM), or sigmoid.

In S42, the position loss value is obtained according to the coordinates ($G_x$, $G_y$) of the initial center point B of the training sample lesion image 1001, the initial length $G_h$, the initial width $G_w$, the coordinates ($P_x$, $P_y$) of the predicted center point A, the predicted length $P_h$, and the predicted width $P_w$.

The position loss value refers to a position loss that exists, when the training sample lesion image 1001 processes the initial image processing model 1, in the process of determining the coordinates ($P_x$, $P_y$) of the predicted center point A, the predicted length $P_h$, the predicted width $P_w$, the coordinates ($G_x$, $G_y$) of the initial center point B, the initial length $G_h$, and initial width $G_w$ of the lesion region. The position loss value is denoted as $L_{al}$.

The position loss value $L_{al}$ may be calculated according to the coordinates ($G_x$, $G_y$) of the initial center point B, the initial length $G_h$, the initial width $G_w$, the coordinates ($P_x$, $P_y$) of the predicted center point A, the predicted length $P_h$, and the predicted width $P_w$.

For example, the position loss value $L_a$ may be calculated according to the following formula (1):

$$L_{al} = \sum_{i \in \{x,y,w,h\}} \text{smooth}_{L_1}(P_i - G_i) \text{ where } \text{smooth}_{L_1}(x) = \begin{cases} 0.5x^2, & (|x| < 1) \\ |x| - 05, & (|x| \geq 1) \end{cases}. \quad (1)$$

In some other embodiments, L1 norm or L2 norm may also be used for a calculation method of the position loss value $L_{al}$.

In S43, a loss value of the training sample lesion image 1001 in the initial image processing model 1 is obtained according to the classification loss value and the position loss value.

After the classification loss value $L_{cls}$ and the position loss value $L_{al}$ are calculated through the above steps, the loss value L may be calculated based on the classification loss value $L_{cls}$ and the position loss value $L_a$. A sum of the classification loss value $L_{cls}$ and the position loss value $L_{al}$ is the loss value L, that is, $L=L_{cls}+L_{al}$.

Figure 10:
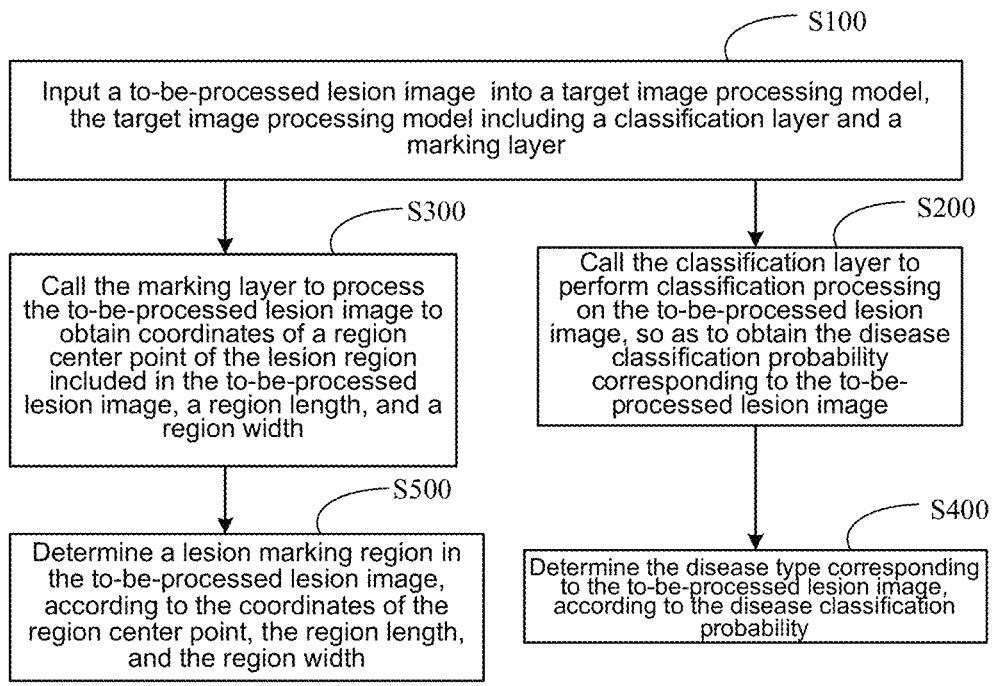
FIG. 10 is a flow diagram of an image processing method, in accordance with some embodiments.

Some embodiments of the present disclosure provide an image processing method. As shown in FIG. 10, the method includes steps 100 to 500 (S100 to S500).

Figure 9:
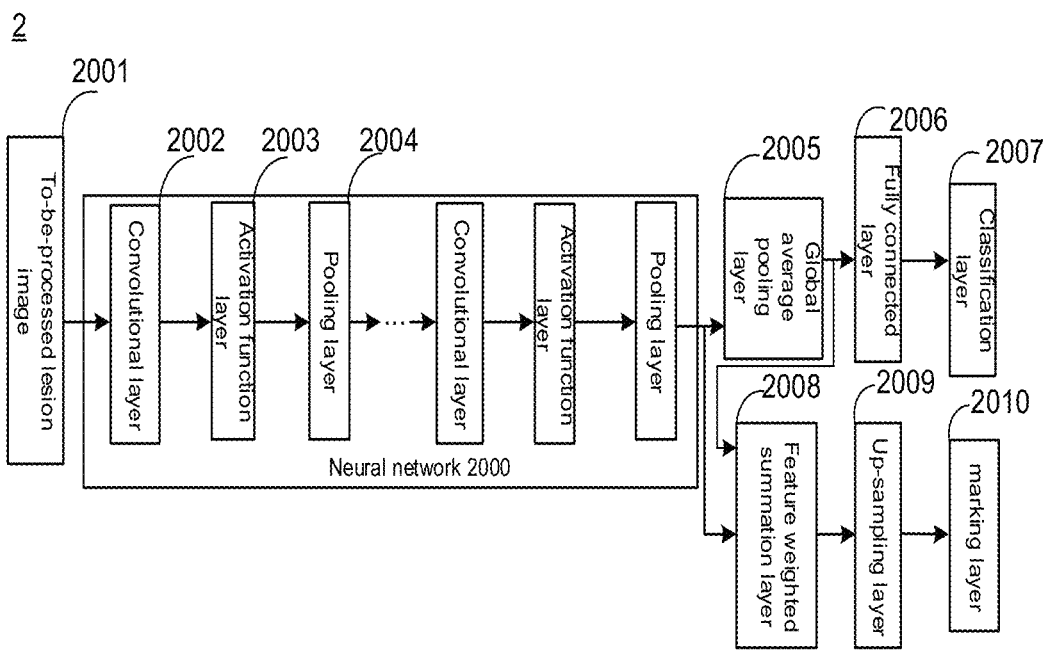
FIG. 9 is a structural diagram of a target image processing model, in accordance with some embodiments.

In S100, a lesion image to be processed 2001 is input into a target image processing model 2 (as shown in FIG. 9).

As shown in FIG. 9, in the embodiments of the present disclosure, the target image processing model 2 is obtained through training by the image processing model generation method of some of the above embodiments. It may be used to process lesion images in the medical field to determine a disease corresponding to the lesion image, and determine a model of a region where the lesion is located in the lesion image.

The lesion image to be processed 2001 refers to an image in the medical field, such as an image captured by a medical instrument.

The target image processing model 2 includes a classification layer 2007 and a marking layer 2010. The classification layer 2007 may be used to perform classification processing on the lesion image to be processed 2001, so as to obtain a classification probability corresponding to the lesion image to be processed 2001, which is used to determine a disease corresponding to the lesion image to be processed 2001. The marking layer 2010 may be used to determine a region where a lesion of the lesion image to be processed 2001 is located in the lesion image. This process will be described in detail in the following steps.

After the lesion image to be processed 2001 is obtained, the lesion image to be processed 2001 may be input into the target image processing model 2, and S200 is performed.

In S200, the classification layer 2007 is called to perform classification processing on the lesion image to be processed 2001, so as to obtain the disease classification probability corresponding to the lesion image to be processed 2001.

The classification layer 2007 is a network layer that may be used to perform classification processing on disease types corresponding to the lesion images, and the classification probabilities of various disease types corresponding to the lesion images may be obtained through the classification layer 2007, thereby obtaining the diseases type corresponding to the lesion images, such as pneumonia, or heart disease.

In S300, the marking layer 2010 is called to process the lesion image to be processed 2001 to obtain coordinates of a region center point, a region length, and a region width of the lesion region included in the lesion image to be processed 2001.

The marking layer 2010 is a network layer that may be used to mark a specific position of a lesion on a pathological tissue, and the marking layer 2010 may add a marking box to a lesion region on a lesion image, for example, the marking box may be a rectangular box, a circular box, or the like.

Figure 11:
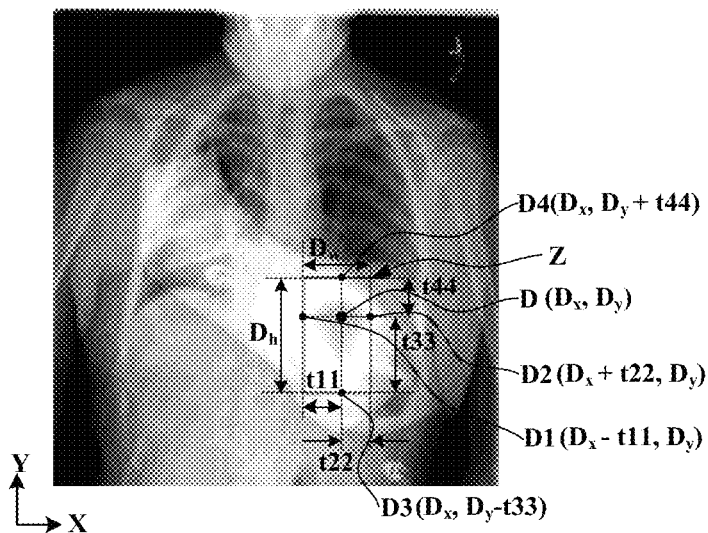
FIG. 11 is a schematic diagram of a lesion image to be processed, in accordance with some embodiments.

As shown in FIG. 11, the lesion image to be processed 2001 is input into the target image processing model 2, and is output out of a lesion box Z after being processed by the marking layer 2010. The lesion box Z is obtained according to coordinates ($D_x$, $D_y$) of a region center point D, a region length $D_h$, and a region width $D_w$. The coordinates ($D_x$, $D_y$) of the region center point D are coordinates of a center point of a lesion region in an image coordinate system corresponding to the lesion image to be processed 2001, and the region length $D_h$ and the region width $D_w$ are a length and a width of the lesion region, respectively.

There is no limitation on the order of performing S200 and S300. S200 and S300 may be performed simultaneously, or S200 is performed firstly and S300 is performed then, or S300 is performed firstly, and S200 is performed then.

After the classification probability of the disease type and region data of the lesion region in the lesion image to be processed 2001 are obtained through S200 and S300, respectively, S400 may be performed.

In S400, the disease type corresponding to the lesion image to be processed 2001 is determined according to the disease classification probability.

The disease classification probability is obtained through S200. If the disease classification probability of a specific disease type in the lesion image to be processed 2001 is within a certain range, it means that the lesion image to be processed 2001 contains the specific disease type. If the disease classification probability of a specific disease type in the lesion image to be processed 2001 is not within a certain range, it means that the lesion image to be processed 2001 do not contain the specific disease type.

In S500, a lesion marking region in the lesion image to be processed 2001 is determined according to the coordinates ($D_x$, $D_y$) of the region center point D, the region length $D_h$, and the region width $D_w$.

The coordinates ($D_x$, $D_y$) of the region center point D obtained in S300 are the coordinates of the center point of the lesion region in the image coordinate system corresponding to the lesion image to be processed 2001; and the region length $D_h$ and the region width $D_w$ are the length and the width corresponding to the lesion region, respectively. A lesion marking region is marked in the lesion image to be processed 2001, as shown by the lesion box Z in FIG. 11.

In the image processing method provided by the embodiments of the present disclosure, the use of the trained image processing model may automatically identify the disease type included in the medical images and mark positions of the lesion regions of various disease types, which saves manpower and improves efficiency. In addition, the generated image processing model has high detection accuracy in classifying and marking the disease type.

In some embodiments, as shown in FIG. 9, the target image processing model 2 further includes a neural network 2000. The neural network 2000 includes at least one layer, and each layer sequentially includes a convolutional layer 2002, an activation function layer 2003, and a pooling layer 2004.

Figure 12:
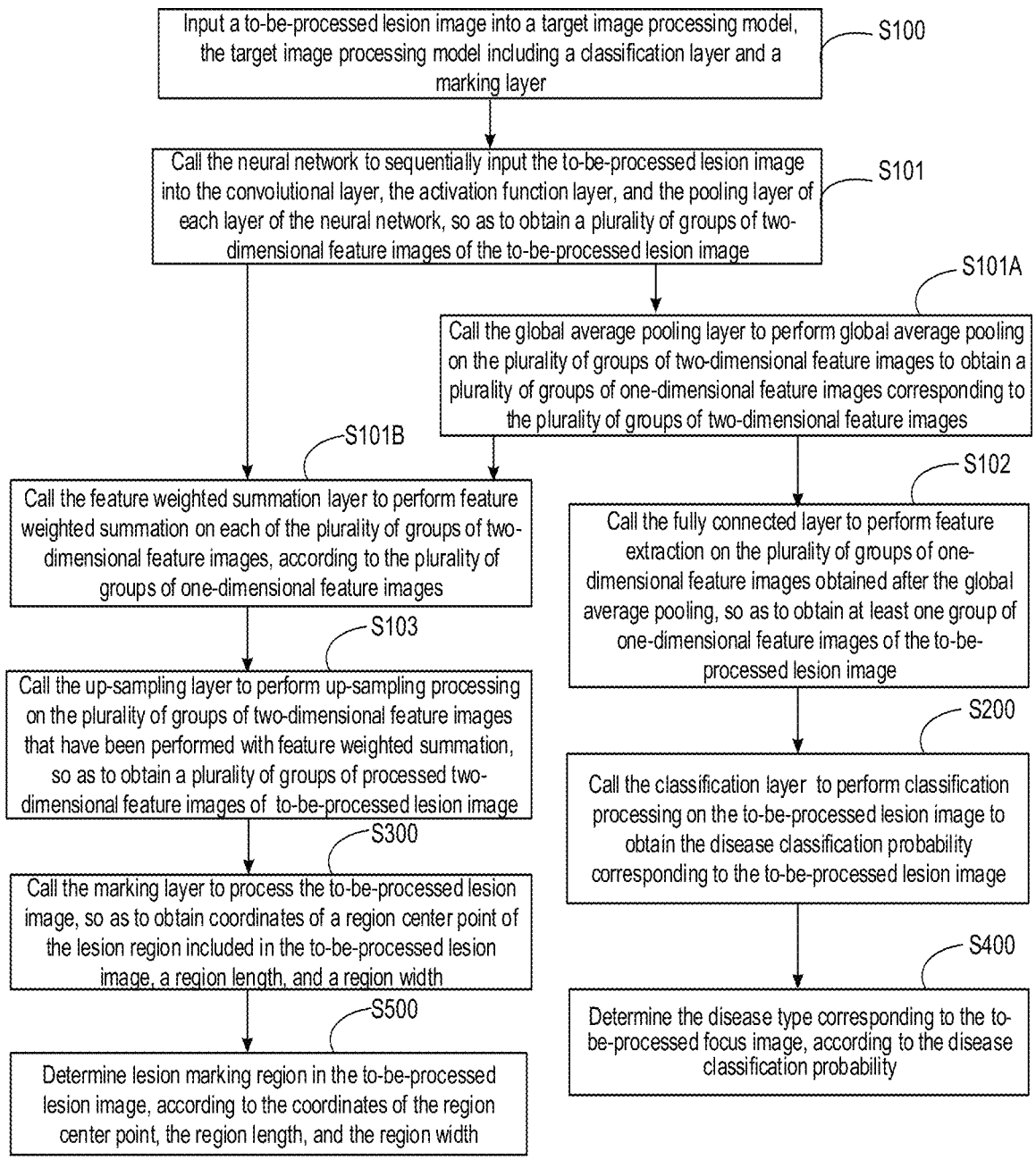
FIG. 12 is a flow diagram of another image processing method, in accordance with some embodiments.

As shown in FIG. 12, the image processing method in the embodiments of the present disclosure further includes: performing step 101 (S101) after S100.

In S101, the neural network 2000 is called to sequentially input the lesion image to be processed 2001 into the convolutional layer 2002, the activation function layer 2003, and the pooling layer 2004 of each layer of the neural network 2000, so as to obtain a plurality of groups of two-dimensional feature maps of the lesion image to be processed 2001.

The convolutional layer 2002 is used to extract features; the activation function layer 2003 is used to activate the extracted features; the pooling layer 2004 is used to downsample the activated features. The plurality of groups of two-dimensional feature maps of the lesion image to be processed 2001 may be obtained through multi-layer superposition.

In some embodiments, the neural network 2000 in the above-mentioned embodiments of the present disclosure may be a convolutional neural network, a recurrent neural network, etc.

In some embodiments, the neural network 2000 in the above-mentioned embodiments of the present disclosure may be a long short term memory network (LSTM), an artificial neural network (ANN), etc.

In some embodiments, as shown in FIG. 9, the target image processing model 2 further includes a global average pooling layer.

As shown in FIG. 12, the image processing method in the embodiments of the present disclosure further includes: performing step 101A (S101A) after S101.

In S101A, the global average pooling layer 2005 is called to perform global average pooling on the plurality of groups of two-dimensional feature maps, so as to obtain a plurality of groups of one-dimensional feature maps corresponding to the plurality of groups of two-dimensional feature maps.

The plurality of groups of two-dimensional feature maps obtained by the lesion image to be processed 2001 through the neural network 2000 are input into the global average pooling layer 2005, and the global average pooling layer 2005 is called to perform global average pooling on the plurality of groups of two-dimensional feature maps to obtain the plurality of groups of one-dimensional feature maps corresponding to the plurality of groups of two-dimensional feature maps.

In some embodiments, as shown in FIG. 9, the target image processing model 2 further includes a fully-connected layer 2006.

As shown in FIG. 12, the image processing method in the embodiments of the present disclosure further includes: performing step 102 (S102) after S101A.

In S102, the fully-connected layer 2006 is called to perform feature extraction on the plurality of groups of one-dimensional feature maps obtained after global average pooling, so as to obtain at least one group of one-dimensional feature maps of the lesion image to be processed 2001.

The plurality of groups of one-dimensional feature maps of the lesion image to be processed 2001 which are obtained through processing of the global average pooling layer 2005 are input into the fully-connected layer 2006. The fully-connected layer 2006 is called to perform feature extraction on the plurality of groups of one-dimensional feature maps obtained after global average pooling, so as to obtain the at least one group of one-dimensional feature maps of the lesion image to be processed 2001. The at least one group of one-dimensional feature maps are input into the classification layer 2007.

Figure 13:
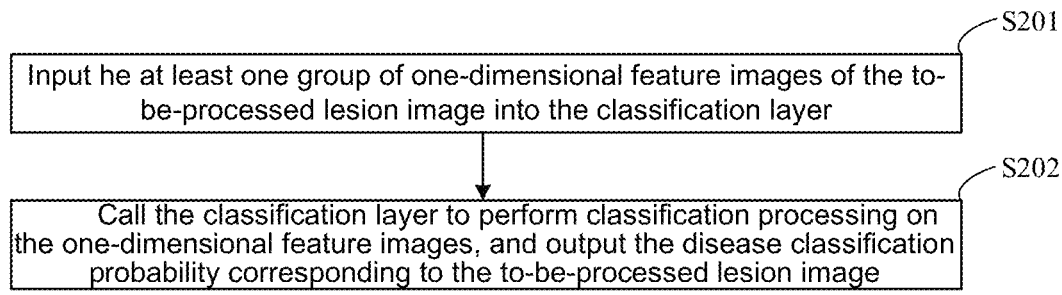
FIGS. 13 to 15 are flow diagrams of S200, S300, and S300 respectively in an image processing method, in accordance with some embodiments.

In some embodiments, as shown in FIG. 13, that the classification layer 2007 is called to perform classification processing on the lesion image to be processed 2001 to obtain the disease classification probability corresponding to the lesion image to be processed 2001 in S200 includes steps 201 to 202 (S201 to S202).

In S201, the at least one group of one-dimensional feature maps of the lesion image to be processed 2001 is input into the classification layer 2007.

In S202, the classification layer 2007 is called to perform classification processing on the one-dimensional feature maps, and to output the disease classification probability corresponding to the lesion image to be processed 2001.

In some embodiments, as shown in FIG. 9, the target image processing model 2 further includes a feature weighted summation layer 2007 and an up-sampling layer 2009.

As shown in FIG. 12, the image processing method in the embodiments of the present disclosure further includes: performing step 101B (S101B) after S101.

In S101B, the feature weighted summation layer 2008 is called to perform, according to the plurality of groups of one-dimensional feature maps, feature weighted summation on each of the plurality of groups of two-dimensional feature maps.

The plurality of groups of two-dimensional feature maps of the lesion image to be processed 2001 and the plurality of groups of one-dimensional feature maps obtained after global average pooling are input into the feature weighted summation layer 2008. The feature weighted summation layer 2008 is called to perform, according to the plurality of groups of one-dimensional feature maps, feature weighted summation on each of the plurality of groups of two-dimensional feature maps.

Step 103 (S103) is performed after S101B.

In S103, the up-sampling layer 2009 is called to perform up-sampling processing on the plurality of groups of two-dimensional feature maps that have been performed with the feature weighted summation to obtain a plurality of groups of processed two-dimensional feature maps of the lesion image to be processed 2001, and called to input the plurality of groups of processed two-dimensional feature maps are into the marking layer 2010.

Figure 14:
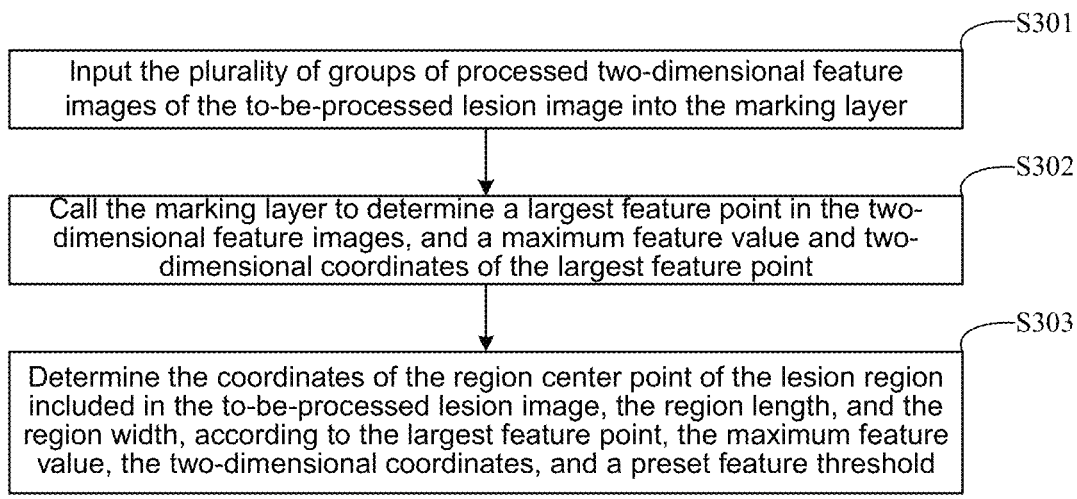

In some embodiments, as shown in FIG. 14, S300 includes steps 301 to 303 (S301 to S303). In S300, the marking layer 2010 is called to process the lesion image to be processed 2001 to obtain coordinates ($D_x$, $D_y$) of a region center point D, a region length $D_h$, a region width $D_w$ of the lesion region included in the lesion image to be processed 2001.

In S301, the plurality of groups of processed two-dimensional feature maps of the lesion image to be processed 2001 are input into the marking layer 2010.

In S302, the marking layer 2010 is called to determine a largest feature point in the two-dimensional feature maps, and a maximum feature value and two-dimensional coordinates of the largest feature point.

In S303, the coordinates ($D_x$, $D_y$) of the region center point D of the lesion region included in the lesion image to be processed 2001, the region length $D_h$, and the region width $D_w$ are determined according to the largest feature point, the maximum feature value, the two-dimensional coordinates, and a preset feature threshold.

The preset feature threshold may be adjusted according to expected ranges of the region length $D_h$ and the region width $D_w$ of the lesion region. In general, the larger the preset feature threshold is, the larger the region length $D_h$ and the region width $D_w$ of the lesion region that are obtained will be, and vice versa.

Figure 15:
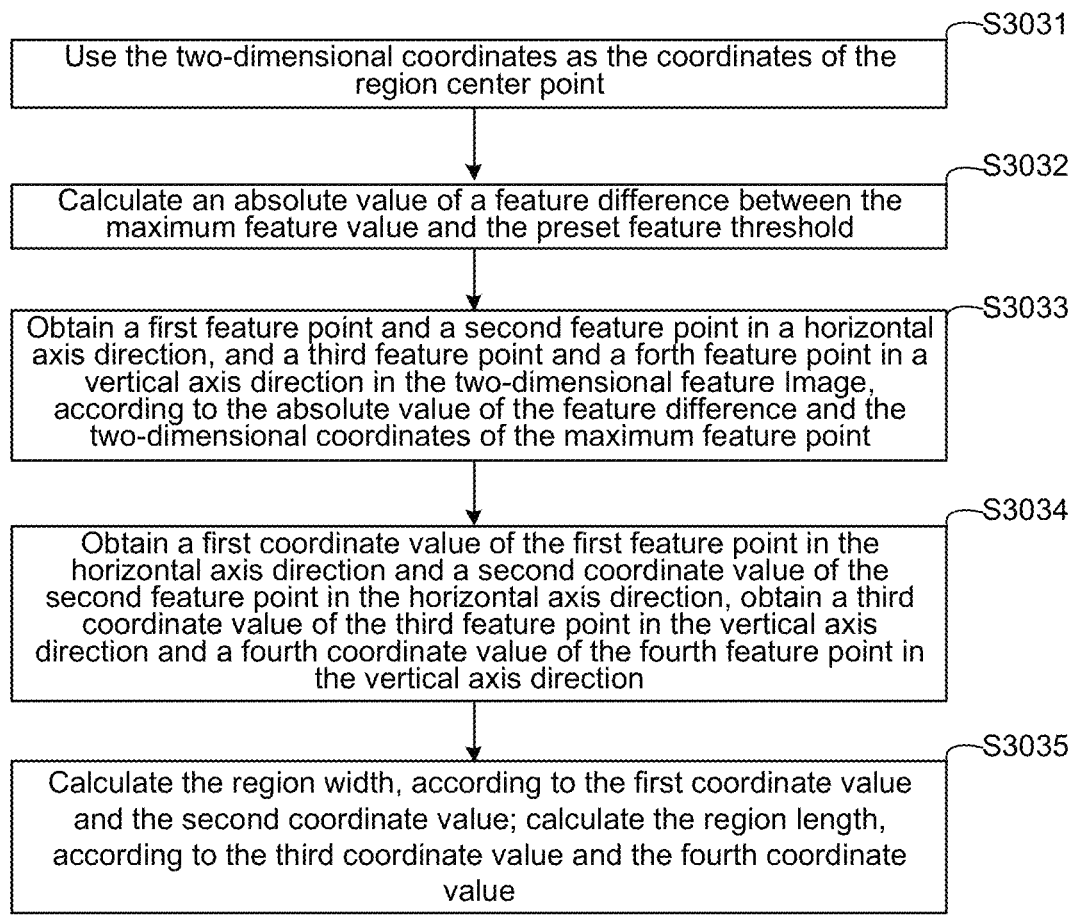

For example, as shown in FIGS. 11 and 15, in S303, that the coordinates ($D_x$, $D_y$) of the region center point D, the region length $D_h$, and the region width $D_w$ of the lesion region included in the lesion image to be processed 2001 are determined according to the largest feature point, the maximum feature value, the two-dimensional coordinates, and a preset feature threshold includes steps 3031 to 3035 (S3031 to S3035).

As shown in FIG. 15, in S3031, the two-dimensional coordinates of the largest feature point are used as the coordinates ($D_x$, $D_y$) of the region center point D.

In S3032, an absolute value of a feature difference between the maximum feature value and the preset feature threshold is calculated.

In S3033, a first feature point D1 and a second feature point D2 in a horizontal axis X direction in the two-dimensional feature map, and a third feature point D3 and a forth feature point D4 in a vertical axis Y direction in the two-dimensional feature map are obtained according to the absolute value of the feature difference and the two-dimensional coordinates of the largest feature point.

In S3034, a first coordinate ($D_x$−t11) of the first feature point D1 in the horizontal axis X direction and a second coordinate ($D_x$+t22) of the second feature point D2 in the horizontal axis X direction are obtained, and both t11 and t22 are not less than zero. A third coordinate ($D_y$−t33) of the third feature point D3 in the vertical axis Y direction and a fourth coordinate ($D_y$+t44) of the fourth feature point D4 in the vertical axis Y direction are obtained, and both t33 and t44 are not less than zero.

In S3035, the region width $D_w$ ($D_w$=t22+t11) is calculated according to the first coordinate ($D_x$−t11) and the second coordinate ($D_x$+t22); and the region length $D_h$ ($D_h$=t44+t33) is calculated according to the third coordinate ($D_y$−t33) and the fourth coordinate ($D_y$+t44).

Figure 16:
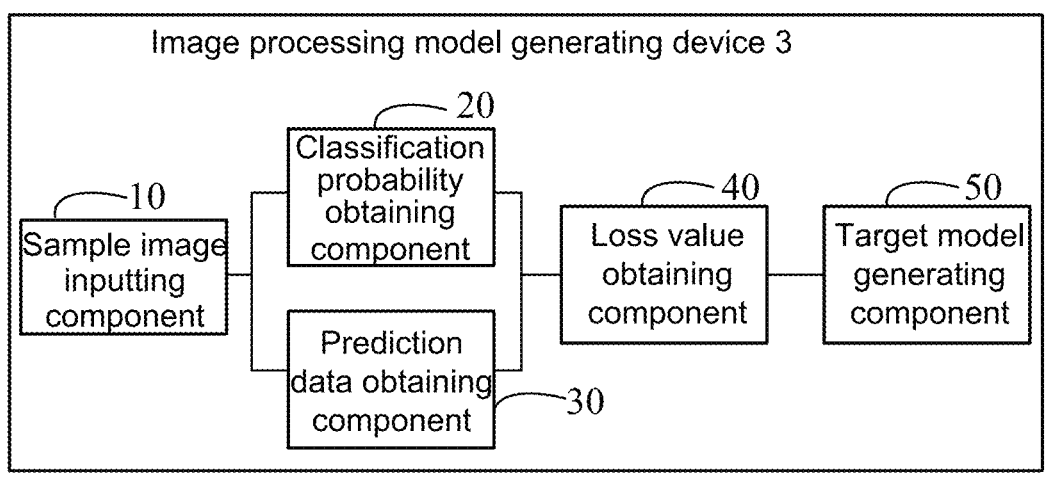
FIG. 16 is a structural diagram of an image processing model generation device, in accordance with some embodiments.

As shown in FIG. 16, some embodiments of the present disclosure provide an image processing model generation device 3, and the image processing model generation device 3 includes:

Please refer to FIGS. 2, 3, and 9. The sample image inputting component 10 is configured to input at least one training sample lesion image 1001 of a known disease type into an initial image processing model 1. The initial image processing model 1 includes a classification layer 1007 and a marking layer 1010. The training sample lesion image 1001 includes coordinates ($G_x$, $G_y$) of an initial center point B of a lesion region, an initial length $G_h$ of the region, and an initial width $G_w$ of the region.

The classification probability obtaining component 20 is coupled to the sample image inputting component 10, and configured to call the classification layer 1007 to perform classification processing on the training sample lesion image 1001, so as to obtain a classification probability of the known disease type corresponding to the training sample lesion image 1001.

The prediction data obtaining component 30 is coupled to the sample image inputting component 10, and configured to call the marking layer 1010 to process the training sample lesion image 1001, so as to obtain coordinates ($P_x$, $P_y$) of a predicted center point A of the lesion region included in the training sample lesion image 1001, a predicted length $P_h$ of the lesion region, and a predicted width $P_w$ of the lesion region.

The loss value obtaining component 40 is coupled to the classification probability obtaining component 20 and the prediction data obtaining component 30, and configured to obtain a loss value L of the at least one training sample lesion image 1001 in the initial image processing model 1 according to the classification probability, the coordinates ($G_x$, $G_y$) of the initial center point B of the at least one training sample lesion image 1001, the initial length $G_h$, the initial width $G_w$, the coordinates ($P_x$, $P_y$) of the predicted center point A, the predicted length $P_h$, and the predicted width $P_w$; and A target model generating component 50 is coupled to the loss value obtaining component 40. The target model generating component 50 is configured to determine whether the loss value L is within a preset range; if the loss value L is not within the preset range, to update parameters of the initial image processing model; and to continue training the image processing model with updated parameters until the loss value L is within the preset range. The image processing model with the updated parameters are used as an initial image processing model of next training, and an image processing model in the last training is used as a target image processing model.

In some embodiments, as shown in FIG. 3, the initial image processing model 1 further includes a neural network 1000, a global average pooling layer 1005, a fully-connected layer 1006, a feature weighted summation layer 1008, and an up-sampling layer 1009. The neural network 1000 includes at least one layer, and each layer sequentially includes a convolutional layer 1002, an activation function layer 1003, and a pooling layer 1004.

Figure 17:
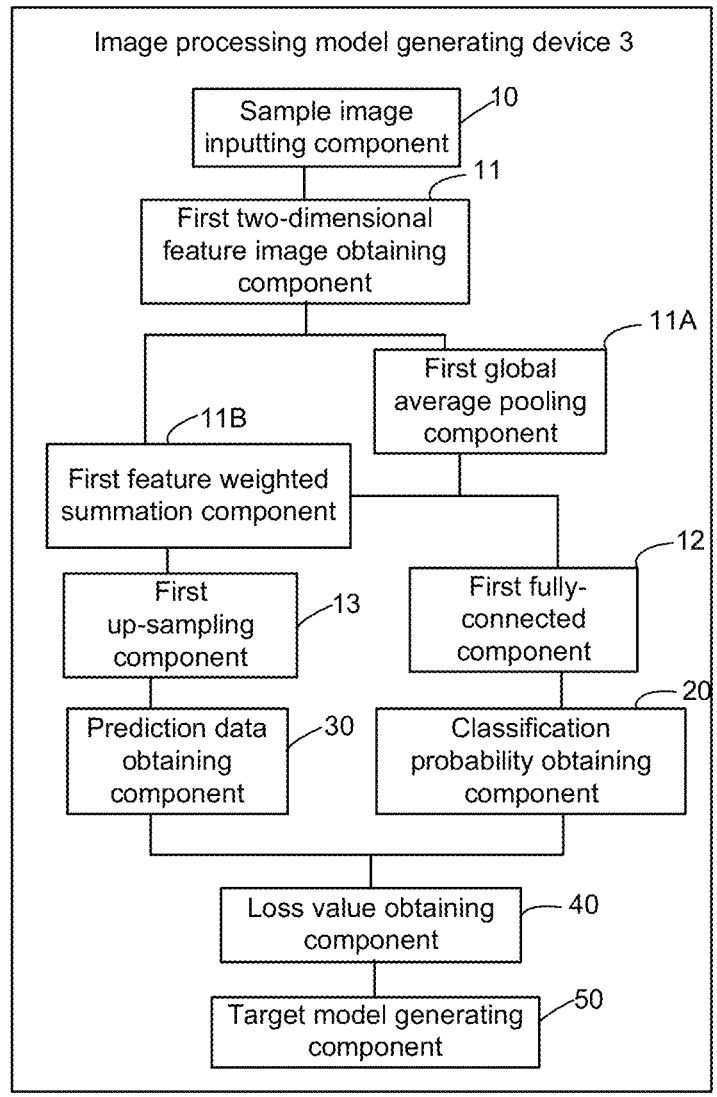
FIG. 17 is a structural diagram of another image processing model generation device, in accordance with some embodiments.

Based on this, as shown in FIG. 17, the image processing model generation device 3 in the embodiments of the present disclosure further includes:

a first two-dimensional feature map obtaining component 11 coupled to the sample image inputting component 10, and configured to call the neural network 1000 to sequentially input the training sample lesion image 1001 into the convolutional layer 1002, the activation function layer 1003, and the pooling layer 1004 of each layer of the neural network 1000, so as to obtain a plurality of groups of two-dimensional feature maps of the training sample lesion image 1001;

a first global average pooling component 11A coupled to the first two-dimensional feature map obtaining component 11, and configured to call the global average pooling layer 1005 to perform global average pooling on the plurality of groups of two-dimensional feature maps, so as to obtain a plurality of groups of one-dimensional feature maps corresponding to the plurality of groups of two-dimensional feature maps;

a first fully-connected component 12 coupled to the first global average pooling component 11A, the first fully-connected component 12 being also coupled to the classification probability obtaining component 20, being configured to call the fully-connected layer 1006 to perform feature extraction on the plurality of groups of one-dimensional feature maps to obtain at least one group of one-dimensional feature maps of the training sample lesion image 1001, being configured to input the at least one group of one-dimensional feature maps into the classification probability obtaining to component 20;

a first feature weighted summation component 11B coupled to the first two-dimensional feature map obtaining component 11 and the first global average pooling component 11A, and configured to call the feature weighted summation layer 1008 to perform feature weighted summation on each of the plurality of groups of two-dimensional feature maps according to the plurality of groups of one-dimensional feature maps; and a first up-sampling component 13 coupled to the first feature weighted summation component 11B, the first up-sampling component 13 being also coupled to the prediction data obtaining component 30; the first up-sampling component 13 being configured to call the up-sampling layer 1009 to perform up-sampling processing on the plurality of groups of two-dimensional feature maps that have been performed with the feature weighted summation, and to input the plurality of groups of two-dimensional feature maps that have been performed with the up-sampling processing into the prediction data obtaining component 30.

Functions of the components included in the image processing model generation device 3 provided by the above-mentioned embodiments of the present disclosure may refer to the description of the corresponding steps in the image processing model generation method described in the aforementioned embodiments.

The image processing model generation device 3 provided in the above-mentioned embodiments of the present disclosure may generate a target image processing model 2. In a case where the target image processing model 2 is applied to a process of identifying the medical images, the target image processing model 2 can automatically detect the disease type and the lesion positions in the medical images, which saves manpower and improves the efficiency of disease diagnosis. In addition, the identification of the disease type and the annotation of the lesion positions in the medical images through the target image processing model 2 are accurate.

Figure 18:
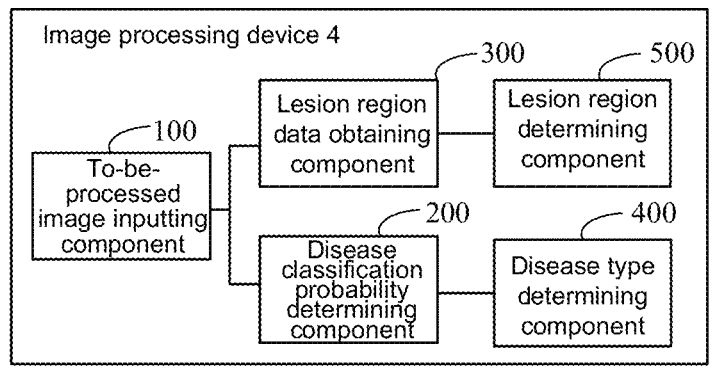
FIG. 18 is a structural diagram of an image processing device, in accordance with some embodiments.

As shown in FIG. 18, some embodiments of the present disclosure further provide an image processing device 4. The image processing device 4 includes:

a to-be-processed-image inputting component 100 configured to input a lesion image to be processed 2001 into a target image processing model 2, the target image processing model 2 being obtained through training by the image processing model generation method in some of the above embodiments of the present disclosure, and the target image processing model 2 including a classification layer 2007 and a mark layer 2010 (as shown in FIG. 9);

a disease classification probability obtaining component 200 coupled to the to-be-processed-image inputting component 100, and configured to call the classification layer 2007 to perform classification processing on the lesion image to be processed 2001, so as to obtain a disease classification probability corresponding to the lesion image to be processed 2001;

a lesion region data obtaining component 300 coupled to the to-be-processed-image inputting component 100, and configured to call the marking layer 2010 to process the lesion image to be processed 2001, so as to obtain coordinates ($D_x$, $D_y$) of a region center point D of a lesion region included in the lesion image to be processed 2001 (as shown in FIG. 11), a region length $D_h$ of the lesion region, and a region width $D_w$ of the lesion region;

a disease type determining component 400 coupled to the disease classification probability obtaining component 200, and configured to determine the disease type corresponding to the lesion image to be processed 2001 according to the disease classification probability; and a lesion region determining component 500 coupled to the lesion region data obtaining component 300, and configured to determine a lesion marking region in the lesion image to be processed 2001 according to the coordinates ($D_x$, $D_y$) of the region center point D, the region length $D_h$, and the region width $D_w$.

In some embodiments, as shown in FIG. 9, the target image processing model 2 further includes a neural network 2000, a global average pooling layer 2005, a fully-connected layer 2006, a feature weighted summation layer 2008, and an up-sampling layer 2009. The neural network 2000 includes at least one layer, and each layer sequentially includes a convolutional layer 2002, an activation function layer 2003, and a pooling layer 2004.

Figure 19:
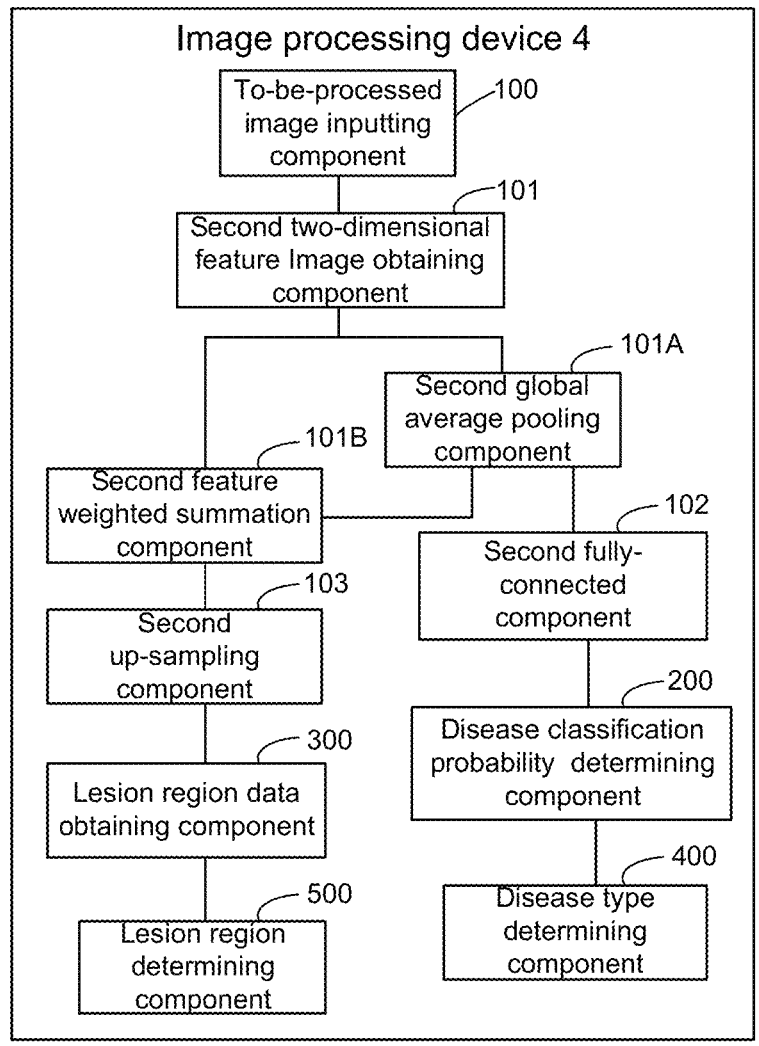
FIG. 19 is a structural diagram of another image processing device, in accordance with some embodiments.

As shown in FIG. 19, the image processing device 4 in the embodiments of the present disclosure further includes:

a second two-dimensional feature map obtaining component 101 coupled to the to-be-processed-image inputting component 100, and configured to call the neural network 2000 to sequentially input the lesion image to be processed 2001 into the convolutional layer 2002, the activation function layer 2003, and the pooling layer 2004 of each layer of the neural network 2000, so as to obtain the plurality of groups of two-dimensional feature maps of the lesion image to be processed 2001;

a second global average pooling component 101A coupled to the second two-dimensional feature map obtaining component 101, and configured to call the global average pooling layer 2005 to perform global average pooling on the plurality of groups of two-dimensional feature maps, so as to obtain the plurality of groups of one-dimensional feature maps corresponding to the plurality of groups of two-dimensional feature maps;

a second fully-connected component 102 coupled to the second global average pooling component 101A and the disease classification probability obtaining component 200, and configured to call the fully-connected layer 2006 to perform feature extraction on the plurality of groups of one-dimensional feature maps, so as to obtain at least one group of one-dimensional feature maps of the lesion image to be processed 2001, and to input the at least one group of one-dimensional feature maps into the disease classification probability obtaining component 200;

a second feature weighted summation component 101B coupled to the second two-dimensional feature map obtaining component 101 and the second global average pooling component 101A, and configured to call the feature weighted summation layer 2008 to perform, according to the plurality of groups of one-dimensional feature maps, feature weighted summation on each of the plurality of groups of two-dimensional feature maps; and a second up-sampling component 103 coupled to the second feature weighted summation component 101B and the lesion region data obtaining component 300, and configured to call the up-sampling layer 2009 to perform up-sampling processing on a plurality of groups of two-dimensional feature maps that have been performed with the feature weighted summation, and to input the plurality of groups of two-dimensional feature maps that have been performed with the up-sampling processing into the lesion region data obtaining component 300.

In the image processing device 4 provided in the above-mentioned embodiments of the present disclosure, the target image processing model 2 is applied to the recognition of medical images, and can automatically detect the disease type and the lesion positions of the medical images, which saves manpower and improves the efficiency of disease diagnosis. In addition, the identification of the disease type in the medical images and the annotation of the lesion positions in the medical images carried to out through the target image processing model 2 are accurate.

Some embodiments of the present disclosure provide a computer-readable storage medium (for example, a non-transitory computer-readable storage medium) in which computer program instructions are stored. When run on a processor, the computer program instructions cause the processor to perform one or more steps in the image processing model generation method as described in some of the above embodiments, and/or one or more steps in the image processing method as described in some of the above embodiments.

For example, the computer-readable storage medium may include, but is not limited to: magnetic storage devices (such as hard disks, floppy disks, or magnetic tapes), optical disks (such as compact disk (CD), and digital versatile disk (DVD)), smart cards, and flash memory devices (such as erasable programmable read-only memory (EPROM), cards, rods or key drivers).

Various computer-readable storage media described in the present disclosure may represent one or more devices and/or other machine-readable storage media used to store information. The term "machine-readable storage media" may include, but are not limited to: wireless channels and various other media capable of storing, containing, and/or carrying instructions and/or data.

Some embodiments of the present disclosure further provide a computer program product. The computer program product includes computer program instructions, and when executed on a computer, the computer program instructions cause the computer to perform one or more steps in the image processing model generation method as described in some of the above embodiments, and/or one or more steps in the image processing method as described in some of the above embodiments.

Some embodiments of the present disclosure further provide a computer program. When executed on a computer, the computer program causes the computer to perform one or more steps in the image processing model generation method as described in some of the above embodiments, and/or one or more steps in the image processing method as described in some of the above embodiments.

Beneficial effects of the computer-readable storage medium, the computer program product, and the computer program are same as beneficial effects of the image processing model generation method and the image processing method described in some of the above embodiments, and will not be repeated herein.

Some embodiments of the present disclosure further provide an electronic device that includes a processor, a memory, and a computer program stored in the memory and executable on the processor. When executing the computer program, the processor implements the image processing model generation method as described in some of the above embodiments, and/or the image processing method as described in some of the above embodiments.

The processor is used to support the image processing model generation device 3, and/or the image processing device 4 described above to perform one or more steps in the image processing model generation method as described in some of the above embodiments, and/or one or more steps in the image processing method as described in some of the above embodiments, and/or other processes in the technique described herein.

The processor may be a central processing unit (CPU), and may also be other general-purpose processors, a digital signal processor (DSP), an application specific integrated circuit (ASIC), a field programmable gate array (FPGA), or other programmable logic devices, discrete gates or transistor logic devices, discrete hardware components, etc. The general-purpose processor may be a microprocessor or to the processor may also be any conventional processor.

The memory is used to store a program code and data of the image processing model generation device 3, and/or a program code and data of the image processing device 4 that are provided by the embodiments of the present disclosure. The processor may execute various functions of the image processing model generation device 3, and/or various functions of the image processing device 4 by running or executing a software program stored in the memory and calling data stored in the memory.

The memory may be a read-only memory (ROM) or another type of static storage device that may store static information and instructions, a random access memory (RAM), or another type of dynamic storage device that may store information and instructions, or an electrically erasable programmable read-only memory (EEPROM), a compact disc read-only memory (CD-ROM) or another compact disc storage, an optical disc storage (including compressed discs, laser discs, optical discs, digital universal discs, and Blu-ray discs), a magnetic disk storage medium or another magnetic storage devices, or any other medium that may be used to carry or store a desired program code in the form of instructions or data structures and can be accessed by a computer, which is not limited thereto. The memory may be separate and connected to the processor via a communication bus. The memory may also be integrated with the processor.

Various embodiments in the present description are described in a progressive manner. Each embodiment focuses on differences between the embodiment and other embodiments, and as for the same or similar parts between the various embodiments, reference may be made to each other.

For the aforementioned method embodiments, for simple description, they are all expressed as a series of action combinations, but those skilled in the art should know that the present disclosure is not limited by the described sequence of actions, because according to the present disclosure, some steps may be performed in other sequences or performed simultaneously. Secondly, those skilled in the art should also know that the embodiments described in the description are all preferred embodiments, and the involved actions and modules are not necessarily required by the present disclosure.

Various embodiments in the present description are described in a progressive manner. Each embodiment focuses on differences between the embodiment and other embodiments, and as for the same or similar parts between the various embodiments, reference may be made to each other. The foregoing descriptions are merely specific implementation manners of the present disclosure, but the protection scope of the present disclosure is not limited thereto, and changes or replacements that any person skilled in the art could conceive of within the technical scope disclosed by the present disclosure should be within the protection scope of the present disclosure. Therefore, the protection scope of the present disclosure should be subject to the protection scope of the claims.

What is claimed is:

1. An image processing model generation method, comprising:
   inputting at least one training sample lesion image of at least one known disease type into an initial image processing model, wherein the initial image processing model includes a classification layer and a marking layer, and each training sample lesion image includes coordinates of an initial center point of a lesion region in the training sample lesion image, an initial length of the lesion region, and an initial width of the lesion region;
   calling the classification layer to perform classification processing on the training sample lesion image, so as to obtain a classification probability of a known disease type corresponding to the training sample lesion image;
   calling the marking layer to process the training sample lesion image, so as to obtain coordinates of a predicted center point of the lesion, a predicted length of the lesion region, and a predicted width of the lesion region;
   obtaining a loss value of the at least one training sample lesion image in the initial image processing model, according to the classification probability corresponding to the training sample lesion image, the coordinates of the initial center point, the initial length, the initial width, the coordinates of the predicted center point, the predicted length, and the predicted width; and
   determining whether the loss value is within a preset range; if the loss value is not within the preset range, updating parameters of the initial image processing model, wherein an image processing model with updated parameters is used as an initial image processing model in next training; and
   above steps are repeated until the loss value is within the preset range, and an image processing model in last training is used as a trained target image processing model.

2. The method according to claim 1, wherein calling the classification layer to perform classification processing on the training sample lesion image, so as to obtain the classification probability of the known disease type corresponding to the training sample lesion image includes:
   inputting at least one group of one-dimensional feature maps of the training sample lesion image into the classification layer;
   calling the classification layer to perform classification processing on the one-dimensional feature maps, and to output the classification probability of the known disease type corresponding to the training sample lesion image.

3. The method according to claim 2, wherein calling the marking layer to process the training sample lesion image, so as to obtain the coordinates of the predicted center point of the lesion region, the predicted length of the lesion region, and the predicted width of the lesion region includes:
   inputting a plurality of groups of processed two-dimensional feature maps of the training sample lesion image into the marking layer;
   calling the marking layer to determine a largest feature point in the two-dimensional feature maps, and a maximum feature value and two-dimensional coordinates of the largest feature point; and determining the coordinates of the predicted center point of the lesion region, the predicted length of the lesion region, and the predicted width of the lesion region, according to the largest feature point, the maximum feature value, the two-dimensional coordinates, and a preset feature threshold.

4. The method according to claim 3, wherein the two-dimensional coordinates include a first coordinate in a horizontal axis direction and a second coordinate in a vertical axis direction; and determining the coordinates of the predicted center point of the lesion region, the predicted length of the lesion region, and the predicted width of the lesion region, according to the largest feature point, the maximum feature value, the two-dimensional coordinates, and the preset feature threshold includes:

determining the two-dimensional coordinates as the coordinates of the predicted center point;

calculating an absolute value of a feature difference between the maximum feature value and the preset feature threshold;

obtaining a first feature point and a second feature point in the horizontal axis direction of the two-dimensional feature maps, and a third feature point and a fourth feature point in the vertical axis direction of the two-dimensional feature maps, according to the absolute value of the feature difference and the two-dimensional coordinates of the largest feature point;

obtaining a first coordinate of the first feature point in the horizontal axis direction, and a second coordinate of the second feature point in the horizontal axis direction;

obtaining a third coordinate of the third feature point in the vertical axis direction, and a fourth coordinate of the fourth feature point in the vertical axis direction;

calculating the predicted width, according to the first coordinate and the second coordinate; and calculating the predicted length, according to the third coordinate and the fourth coordinate.

5. The method according to claim 3, wherein the initial image processing model further includes a global average pooling layer; and before the classification layer and the marking layer are called, the method further comprises:

inputting a plurality of groups of two-dimensional feature maps of the training sample lesion image into the global average pooling layer; and calling the global average pooling layer to perform global average pooling on the plurality of groups of two-dimensional feature maps, so as to obtain a plurality of groups of one-dimensional feature maps corresponding to the plurality of groups of two-dimensional feature maps.

6. The method according to claim 5, wherein the initial image processing model further includes a fully-connected layer; and after the global average pooling layer is called, and before the classification layer is called, the method further comprises:

calling the fully-connected layer to perform feature extraction on the plurality of groups of one-dimensional feature maps obtained after global average pooling, so as to obtain the at least one group of one-dimensional feature maps of the training sample lesion image; the at least one group of one-dimensional feature maps being input into the classification layer.

7. The method according to claim 5, wherein the initial image processing model further includes a feature weighted summation layer and an up-sampling layer; and after the global average pooling layer is called, and before the marking layer is called, the method further comprises:

inputting the plurality of groups of two-dimensional feature maps of the training sample lesion image, and the plurality of groups of one-dimensional feature maps obtained after global average pooling into the feature weighted summation layer;

calling the feature weighted summation layer to perform, according to the plurality of groups of one-dimensional feature maps, feature weighted summation on each of the plurality of groups of two-dimensional feature maps; and calling the up-sampling layer to perform up-sampling processing on a plurality of groups of two-dimensional feature maps that have been performed with the feature weighted summation, so as to obtain the plurality of groups of processed two-dimensional feature maps of the training sample lesion image; the plurality of groups of processed two-dimensional feature maps being input into the marking layer.

8. The method according to claim 5, wherein the initial image processing model further includes a neural network, the neural network includes at least one layer, and each layer sequentially includes a convolutional layer, an activation function layer, and a pooling layer; and before inputting the plurality of groups of two-dimensional feature maps of the training sample lesion image into the global average pooling layer, the method further comprises:

inputting the training sample lesion image into the neural network; and calling the neural network to sequentially input the training sample lesion image into the convolutional layer, the activation function layer, and the pooling layer of each layer of the neural network, so as to obtain the plurality of groups of two-dimensional feature maps of the training sample lesion image; wherein the plurality of groups of two-dimensional feature maps are input into the global average pooling layer.

9. The method according to claim 2, wherein the initial image processing model further includes a global average pooling layer; and before the classification layer and the marking layer are called, the method further comprises:

inputting a plurality of groups of two-dimensional feature maps of the training sample lesion image into the global average pooling layer; and calling the global average pooling layer to perform global average pooling on the plurality of groups of two-dimensional feature maps, so as to obtain a plurality of groups of one-dimensional feature maps corresponding to the plurality of groups of two-dimensional feature maps.

10. The method according to claim 9, wherein the initial image processing model further includes a neural network, the neural network includes at least one layer, and each layer sequentially includes a convolutional layer, an activation function layer, and a pooling layer; and before inputting the plurality of groups of two-dimensional feature maps of the training sample lesion image into the global average pooling layer, the method further comprises:
inputting the training sample lesion image into the neural network; and
calling the neural network to sequentially input the training sample lesion image into the convolutional layer, the activation function layer, and the pooling layer of each layer of the neural network, so as to obtain the plurality of groups of two-dimensional feature maps of the training sample lesion image; wherein the plurality of groups of two-dimensional feature maps are input into the global average pooling layer.

11. The method according to claim 1, wherein obtaining the loss value of the at least one training sample lesion image in the initial image processing model, according to the classification probability corresponding to the training sample lesion image, the coordinates of the initial center point, the initial length, the initial width, the coordinates of the predicted center point, the predicted length, and the predicted width includes:
calculating a classification loss value, according to the classification probability corresponding to the training sample lesion image;
calculating a position loss value, according to the coordinates of the initial center point, the initial length, the initial width, the coordinates of the predicted center point, the predicted length, and the predicted width that correspond to the training sample lesion image; and
obtaining the loss value of the training sample lesion image in the initial image processing model, according to the classification loss value and the position loss value.

12. An image processing method, comprising:
inputting a lesion image to be processed into a target image processing model; the target image processing model being obtained through training by the method according to claim 1, the target image processing model including the classification layer and the marking layer;
calling the classification layer to perform classification processing on the lesion image to be processed, so as to obtain a classification probability of a disease type corresponding to the lesion image to be processed;
calling the marking layer to process the lesion image to be processed, so as to obtain coordinates of a region center point of a lesion region included in the lesion image to be processed, a region length of the lesion region, and a region width of the lesion region;
determining a disease type corresponding to the lesion image to be processed, according to the classification probability; and
determining a lesion marking region in the lesion image to be processed, according to the coordinates of the region center point, the region length, and the region width.

13. The method according to claim 12, wherein calling the classification layer to perform classification processing on the lesion image to be processed, so as to obtain the classification probability of the disease type corresponding to the lesion image to be processed includes:
inputting at least one group of one-dimensional feature maps of the lesion image to be processed into the classification layer;
calling the classification layer to perform classification processing on the one-dimensional feature maps; and
outputting the classification probability of the disease type corresponding to the lesion image to be processed.

14. The method according to claim 12, wherein calling the marking layer to process the lesion image to be processed, so as to obtain coordinates of the region center point of the lesion region included in the lesion image to be processed, the region length of the lesion region, and a region width of the lesion region includes:
inputting a plurality of groups of processed two-dimensional feature maps of the lesion image to be processed into the marking layer;
calling the marking layer to determine a largest feature point in the two-dimensional feature maps, and a maximum feature value and two-dimensional coordinates of the largest feature point; and
determining the coordinates of the region center point of the lesion region included in the lesion image to be processed, the region length of the lesion region, and the region width of the region, according to the largest feature point, the maximum feature value, the two-dimensional coordinates, and a preset feature threshold.

15. The method according to claim 14, wherein the two-dimensional coordinates include a first coordinate in a horizontal axis direction and a second coordinate in a vertical axis direction; and
determining the coordinates of the region center point of the lesion region included in the lesion image to be processed, the region length of the region, and the region width of the lesion region, according to the largest feature point, the maximum feature value, the two-dimensional coordinates, and the preset feature threshold includes:
determining the two-dimensional coordinates as the coordinates of the region center point;
calculating an absolute value of a feature difference between the maximum feature value and the preset feature threshold;
obtaining a first feature point and a second feature point in the horizontal axis direction of the two-dimensional feature maps, and a third feature point and a fourth feature point in the vertical axis direction of the two-dimensional feature maps, according to the absolute value of the feature difference and the two-dimensional coordinates of the largest feature point;
obtaining a first coordinate of the first feature point in the horizontal axis direction, and a second coordinate of the second feature point in the horizontal axis direction;
obtaining a third coordinate of the third feature point in the vertical axis direction, and a fourth coordinate of the fourth feature point in the vertical axis direction;
calculating the region width, according to the first coordinate and the second coordinate; and
calculating the region length, according to the third coordinate and the fourth coordinate.

16. A non-transitory computer-readable storage medium, storing computer program instructions that, when executed by a processor, cause the processor to perform the image processing method according to claim 12.

17. An electronic device, comprising a processor, a memory, and a computer program that is stored in the memory and executable on the processor;
wherein when the computer program is executed by the processor, the image processing method according to claim 12 is implemented.

18. A non-transitory computer-readable storage medium, storing computer program instructions that, when executed by a processor, cause the processor to perform the image processing model generation method according to claim 1.

19. An electronic device, comprising a processor, a memory, and a computer program that is stored in the memory and executable on the processor;
   wherein when the computer program is executed by the processor, the image processing model generation method according to claim 1 is implemented.

20. The method according to claim 1, wherein calling the marking layer to process the training sample lesion image, so as to obtain the coordinates of the predicted center point of the lesion region, the predicted length of the lesion region, and the predicted width of the lesion region includes:
   inputting a plurality of groups of processed two-dimensional feature maps of the training sample lesion image into the marking layer;
   calling the marking layer to determine a largest feature point in the two-dimensional feature maps, and a maximum feature value and two-dimensional coordinates of the largest feature point; and
   determining the coordinates of the predicted center point of the lesion region, the predicted length of the lesion region, and the predicted width of the lesion region, according to the largest feature point, the maximum feature value, the two-dimensional coordinates, and a preset feature threshold.

* * * * *

UNITED STATES PATENT AND TRADEMARK OFFICE
CERTIFICATE OF CORRECTION

PATENT NO. : 11,887,303 B2
APPLICATION NO. : 17/423439
DATED : January 30, 2024
INVENTOR(S) : Yongming Shi et al.

It is certified that error appears in the above-identified patent and that said Letters Patent is hereby corrected as shown below:

In the Claims

In Column 24, Line 25, please change "lesion" to --lesion region--.

Signed and Sealed this
Ninth Day of April, 2024

Katherine Kelly Vidal
*Director of the United States Patent and Trademark Office*